US008670605B2

(12) United States Patent
Yanai

(10) Patent No.: US 8,670,605 B2
(45) Date of Patent: *Mar. 11, 2014

(54) IDENTIFICATION METHOD OF DATA POINT DISTRIBUTION AREA ON COORDINATE PLANE AND RECORDING MEDIUM

(75) Inventor: Hirokazu Yanai, Osaka (JP)

(73) Assignee: Ricoh Company, Ltd., Tokyo (JP)

( * ) Notice: Subject to any disclaimer, the term of this patent is extended or adjusted under 35 U.S.C. 154(b) by 413 days.

This patent is subject to a terminal disclaimer.

(21) Appl. No.: 13/044,676

(22) Filed: Mar. 10, 2011

(65) Prior Publication Data

US 2011/0231129 A1  Sep. 22, 2011

(30) Foreign Application Priority Data

Mar. 18, 2010  (JP) .................... 2010-061821

(51) Int. Cl.
*G06K 9/00* (2006.01)
(52) U.S. Cl.
USPC ........... 382/141; 382/144; 382/145; 382/147; 382/149; 382/150
(58) Field of Classification Search
USPC ......... 382/141, 144, 145, 146, 147, 148, 149, 382/150, 151
See application file for complete search history.

(56) References Cited

U.S. PATENT DOCUMENTS

| 5,240,866 | A | 8/1993 | Friedman et al. |
| 6,876,445 | B2 | 4/2005 | Shibuya et al. |
| 6,961,466 | B2 | 11/2005 | Imagawa et al. |
| 7,804,980 | B2 | 9/2010 | Sasaki |
| 2009/0000995 | A1 | 1/2009 | Yanai |
| 2010/0110078 | A1 | 5/2010 | Yanai |

FOREIGN PATENT DOCUMENTS

| JP | 6-61314 | 3/1994 |
| JP | 6-348991 | 12/1994 |
| JP | 3659914 | 3/2005 |
| JP | 3709879 | 8/2005 |
| JP | 2006-284447 | 10/2006 |
| JP | 2007-72987 | 3/2007 |
| JP | 4038356 | 11/2007 |
| JP | 2009-10303 | 1/2009 |
| JP | 2010-27910 | 2/2010 |
| JP | 2010-108236 | 5/2010 |
| JP | 2010-129597 | 6/2010 |

*Primary Examiner* — Brian Le
(74) *Attorney, Agent, or Firm* — Cooper & Dunham LLP

(57) ABSTRACT

A disclosed identification method of identifying a data point distribution area on a coordinate plane includes dividing an area on the coordinate plane into divided areas so that the divided areas radiate from a division center point; selecting, in each of the divided areas, from among the data points in the divided area, a data point having the greatest distance from the division center point as a representative point; determining whether there is an overlapping area where a distribution representative point area overlaps a determination area; and determining, when there is the overlapping area, that the data group to be determined is a relevant data group.

16 Claims, 38 Drawing Sheets

IDENTIFICATION METHOD OF DATA POINT DISTRIBUTION AREA ON COORDINATE PLANE AND RECORDING MEDIUM

CROSS-REFERENCE TO RELATED APPLICATIONS

The present application claims priority under 35 U.S.C §119 based on Japanese Patent Application No. 2010-061821 filed Mar. 18, 2010, the entire contents of which are hereby incorporated herein by reference.

BACKGROUND OF THE INVENTION

1. Field of the Invention

The present invention relates to an identification method of determining whether a data point distribution area is distributed in a specific determination area and a recording medium storing a program causing a computer to execute the identification method.

2. Description of the Related Art

Semiconductor devices (a.k.a chips) are manufactured through various processes. Various defects during the various processes may cause the degradation of the quality and the decrease of the yield rate of the semiconductor devices. In this regard, to improve and stabilize the yield rate, the pattern defect inspection and the particle (contamination) inspection are conducted after a predetermined process to check the existence of the defects.

Further, in each process, after the pattern is formed, the electric characteristic test (wafer test) is performed on each chip on the wafer to detect the defects.

Of the information obtained as a result of inspection or test, there is information indicating defects on the wafer and a distribution of defective chips. In the following, the defects on the wafer or the distribution of defective chips is called "defect distribution".

The defect distribution may be classified into two types: in one type, the defect distribution is substantially uniformly distributed across the wafer without being concentrated on a specific area on the wafer; and in the other type, the defect distribution is unevenly distributed and may be concentrated on a specific area on the wafer. The defects in the former type where the defects are evenly distributed may be called random defects. On the other hand, the defects in the latter type where the defects are concentrated on a part of the wafer may be called clustering defects.

The defect distribution in which the defects are concentrated (hereinafter "concentrated defect distribution") is mainly caused by the problems in the manufacturing processes, manufacturing apparatuses and the like. Because of this feature, by investigating the manufacturing processes, the manufacturing apparatuses, and the like, the cause of the lowering of the yield rate may be detected.

As one example of using the information, a status of the defect distribution on a wafer is analyzed first, and based on the analysis, the cause of the defects in the manufacturing processes, manufacturing apparatuses, and the like is estimated (see, for example, Patent Documents 1 and 2).

Patent document 1 describes a method of specifying a cause of defect by grouping (classifying) the wafer based on a status of the clustered defect distribution and then determining whether the status is similar to a known pattern of the defect distribution.

Patent document 2 describes a method of classifying the categories of the defects based on the distribution status of the defect into repetitive defects, congestion defects, liner defects, ring/lump defects, random defects and the like.

Generally, the position of the chip is expressed using the X axis and the Y axis. To express the information of data group indicating the chip positions on a wafer, those data are expressed on the XY rectangular coordinate plane.

As described above, the concentrated defect distribution in the manufacturing process of manufacturing the semiconductor devices may be caused by the problems on the manufacturing apparatus and the like. Therefore, when the concentrated defect distribution is detected, a defective process may be estimated by collecting the information of lots of the wafers having a similar status of the defect distribution and then investigating the relevant recorded data indicating, for example, which processing apparatus was used and when the process was performed in the manufacturing processes.

In this case, whether the defective distribution is similar to the known pattern of the defect distribution is determined depending on whether the defective distribution exists on a specific area on a wafer (coordinate plane).

In the methods of Patent Documents 1 and 2, the position of the defective distribution is specified by processing data indicating the positions of the defects and defective chips. However, all of the data points of the defective distribution have respective data (e.g., positional information). Namely, under a status where all the data points included in the data point distribution area on the coordinate plane have the respective data, it is determined whether the data point distribution area is distributed on a specified determination area set on the coordinate plane.

Patent Document 1: Japanese Patent Application Publication No. 06-61314

Patent Document 2: Japanese Patent No. 4038356

SUMMARY OF THE INVENTION

According to one aspect of the present invention, while the information amount expressing the data point distribution area on the coordinate plane is decreased, it is determined whether the data point distribution area is distributed on a specified determination area set on the coordinate plane.

According to another aspect of the present invention, there is provided an identification method of identifying a data point distribution area on a coordinate plane. The identification method includes a distribution representative point selection step of dividing an area on the coordinate plane into two or more divided areas in a manner such that the divided areas radiate from a division center point, the division center point being an arbitrary point and a center point of the divisions, plural data being expressed as data points on the coordinate plane, the plural data constituting a data group to be determined, each of the plural data including two variables as a pair, the data point distribution area being a distribution area of the data points, and selecting, in each of the divided areas, from among the data points in the divided area, a data point having the greatest distance from the division center point as a representative point of the data point distribution area; and a determination step of determining whether there is an overlapping area where a distribution representative point area overlaps a determination area, the distribution representative point area being defined by connecting the representative points with lines, the determination area being a specific area set on the coordinate plane, and determining, when determining that there is the overlapping area, that the data group to be determined is a relevant data group.

BRIEF DESCRIPTION OF THE DRAWINGS

Other objects, features, and advantages of the present invention will become more apparent from the following description when read in conjunction with the accompanying drawings, in which.

DETAILED DESCRIPTION OF THE PREFERRED EMBODIMENTS

First, an embodiment of the present invention is described with reference to result data of pattern defect.

Figure 1:
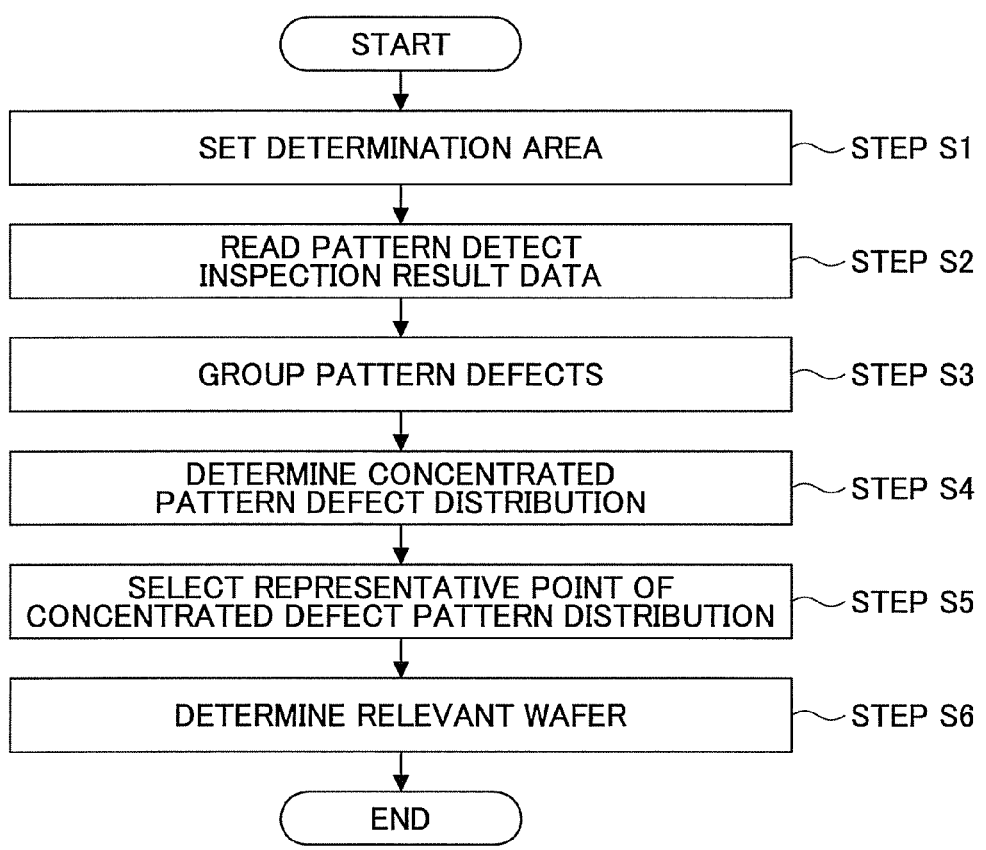
FIG. 1 is a flowchart illustrating a processing procedure of a method according to an embodiment of the present invention.
Figure 2:
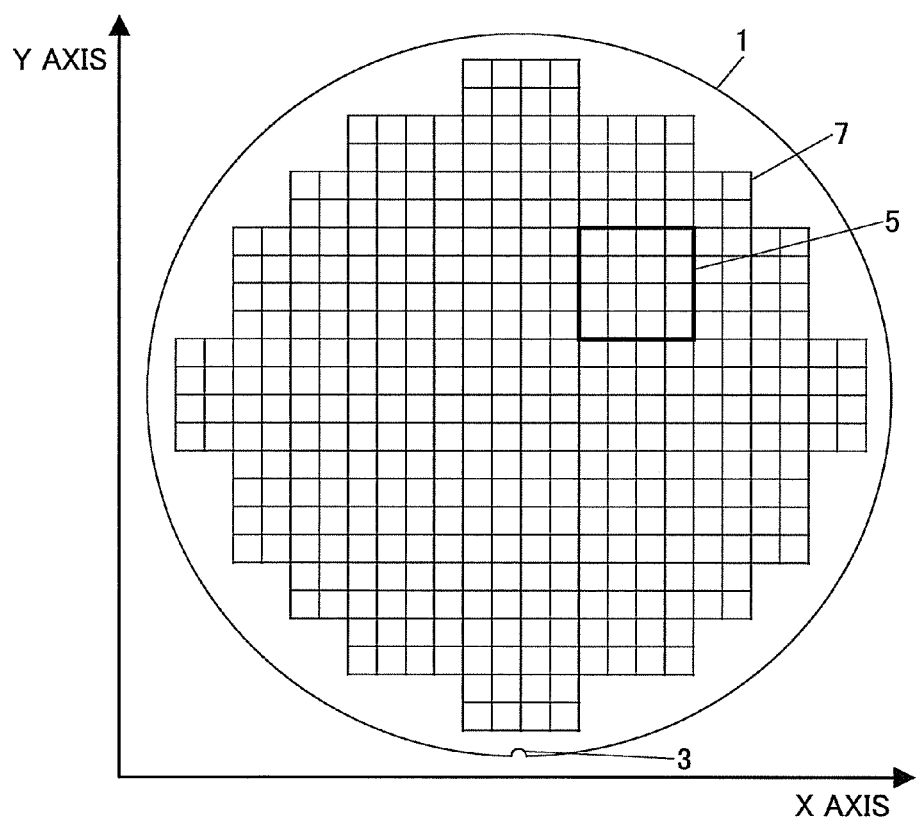
FIG. 2 is a drawing illustrating a determination area set on a wafer.
Figure 3:
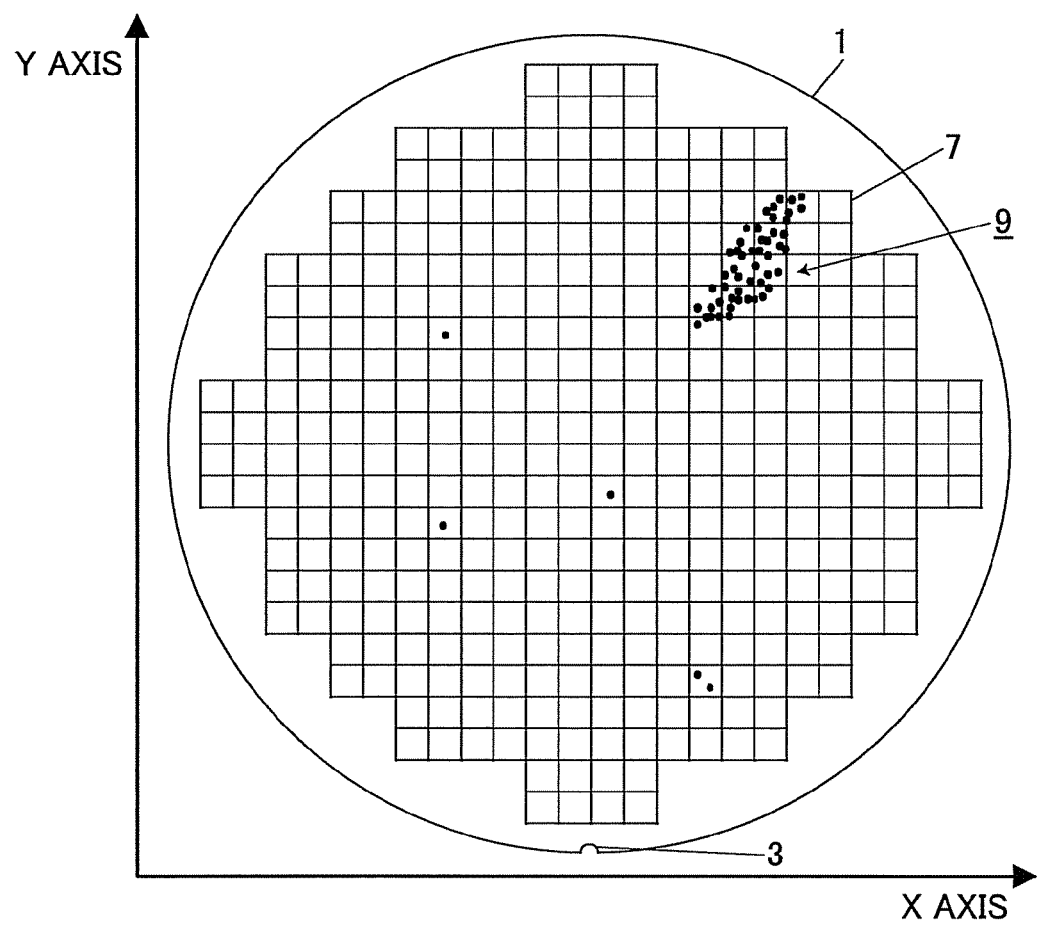
FIG. 3 is a drawing illustrating a concentrated pattern defect distribution on the wafer.
Figure 4:
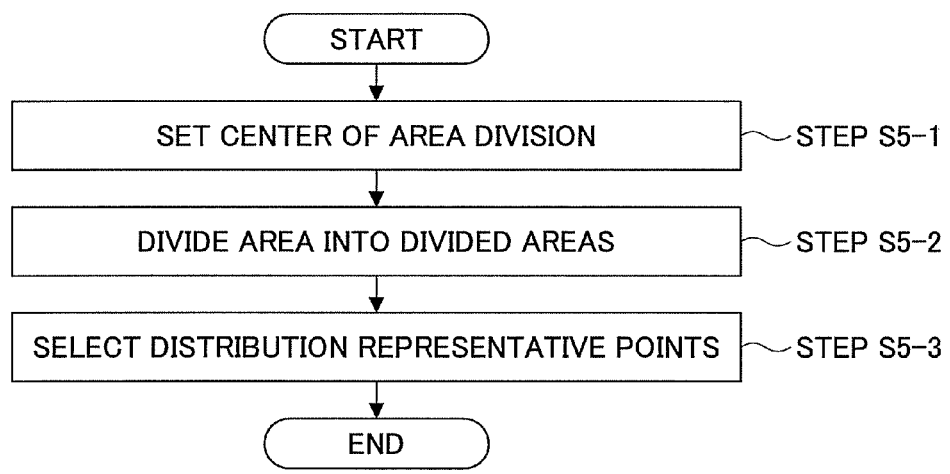
FIG. 4 is a flowchart illustrating a distribution representative point selection step for the concentrated pattern defect distribution.
Figure 5:
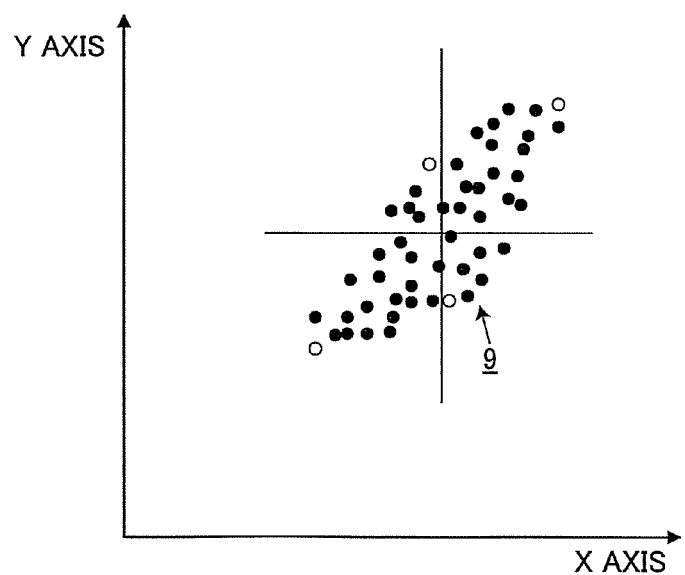
FIG. 5 is an enlarged view of the concentrated pattern defect distribution of FIG. 3, the view including lines dividing the area of the concentrated pattern defect distribution into four (4) areas.
Figure 6:
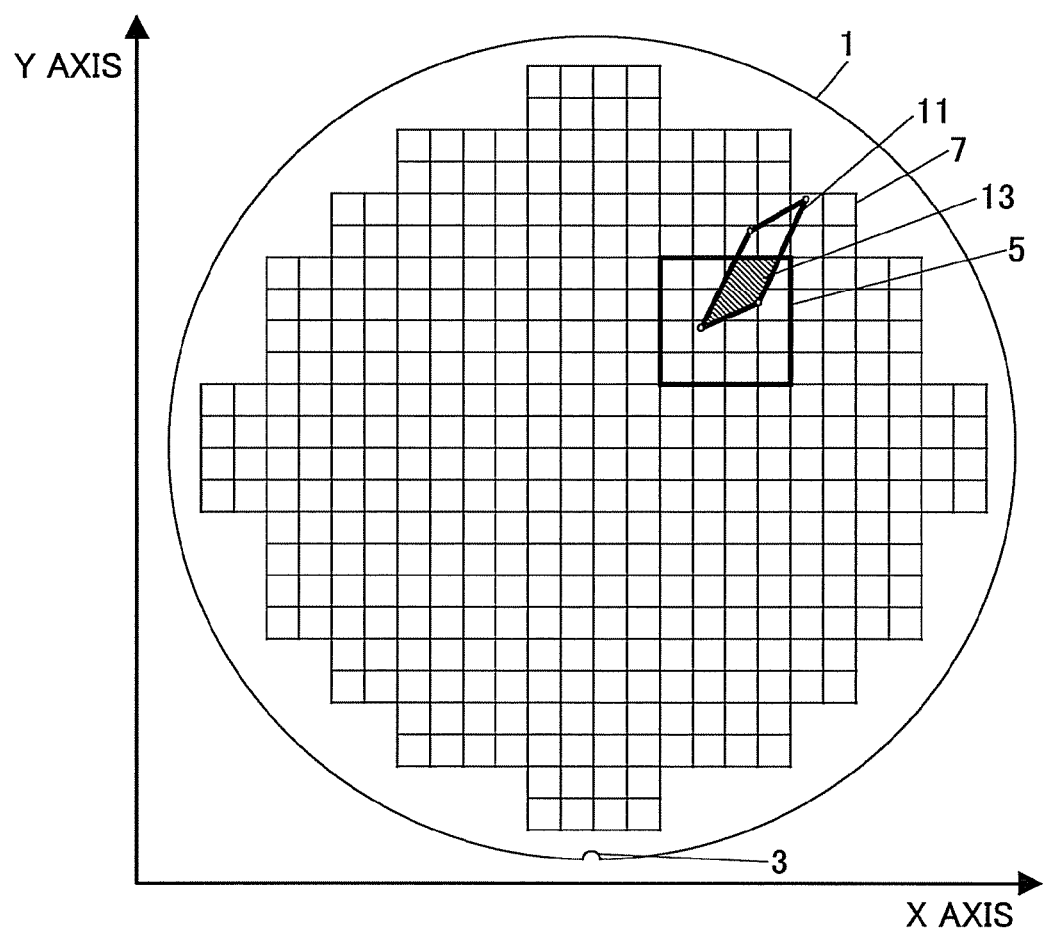
FIG. 6 is a drawing in which the determination area and a concentrated pattern defect distribution representative point area are displayed so as to be overlapped with each other.

FIG. 1 is a flowchart illustrating a method according to an embodiment of the present invention. FIG. 2 illustrates a determination area set on a wafer. FIG. 3 illustrates pattern defect positions on the wafer. FIG. 4 is a flowchart illustrating a distribution representative point selection step of a concentrated pattern defect distribution. FIG. 5 is an enlarged view of a pattern defect group and further illustrates dividing straight lines along the Y axis to divide the area into eight (8) areas. FIG. 6 illustrates the determination area and the concentrated pattern defect representative point area so as to be overlapped with each other on the same coordinate plane. With reference to FIGS. 1 through 6, this embodiment is described.

Step S1: A determination area 5 is set on the coordinate plane of a pattern defect inspection result. Herein, it is assumed that the determination area 5 is set on a part of the upper right-hand side when a wafer 1 is set in a manner such that a notch 3 of the wafer 1 is arranged on the lower side as illustrated in FIG. 2. The notch 3 is a mark on the wafer 1 so that the crystal orientation of the silicon can be recognized. The wafer 1 includes chips 7 arranged in a matrix manner.

Step S2: Next, pattern defect inspection result data associated with target wafer information (i.e., information of the wafer to be determined (inspected)) are read from an inspection apparatus or a database storing the pattern defect inspection result data. The pattern defect inspection result data includes positional coordinate information of pattern defects. FIG. 3 illustrates pattern defect positions on the wafer 1. In FIG. 3, the pattern defects are expressed as dots.

Step S3: Next, the pattern defects are grouped. To that end, for example, mutual distances between the data points representing the pattern defects are obtained. Then, the data points having the mutual distance less than a predetermined threshold value are determined to be included in the same group. However, a method of grouping the data points is not limited to this method, and any other appropriate method may alternatively used.

Step S4: Next, the concentrated pattern defect distribution is selected (determined) from the groups of the pattern defects. To that end, for each of the groups of the pattern defect, it is determined whether the number of the pattern defects is equal to or greater than, for example, five (5). In this case, when determining that the number of the pattern defects is equal to or greater than five (5), the pattern defect group is determined to be the concentrated pattern defect distribution. In this case, the pattern defect group on the upper right-hand side on the wafer of FIG. 3 is determined to be the concentrated pattern defect distribution 9. In this embodiment, the data points included in the concentrated pattern defect distribution 9 are a data group to be determined. However, in this case, all pattern defect data may be treated as the data group to be determined, or only the pattern defect data in a specific area may be treated as the data group to be determined. Further, in this embodiment, the data points included in the concentrated pattern defect distribution 9 are candidates to be selected as the representative points of the data point distribution area.

Step S5: Next, the representative points of the concentrated pattern defect distribution 9 are determined (selected). To that end, plural data points representing the contour (outline) of the distribution area of the concentrated pattern defect distribution 9 are determined (selected) to be the representative points of the concentrated pattern defect distribution 9. With reference to FIGS. 4 and 5, a step of selecting the representative points of the distribution area (hereinafter "distribution representative point selection step") is described.

Step S5-1: A division center point for dividing the distribution area of the concentrated pattern defect distribution 9 is set. In this embodiment, the gravity center of the distribution area of the data points in the concentrated pattern defect distribution 9 is set as the division center point.

Step S5-2: The area is divided into divided areas in a manner such that the divided areas radiate from the division center point. In this embodiment, as the lines for dividing the area into divided areas, a line that passes through the division center point and that is parallel to the X axis and a line that passes through the division center point and that is parallel to the Y axis are used, so that the area is divided into four (4) divided areas (see FIG. 5).

Step S5-3: In each of the divided areas, the data point having the longest distance from the division center point is selected as the representative point of the concentrated pattern defect distribution 9. In FIG. 5, the data points of the representative points are displayed in white circles, and the data points other than the representative points are displayed in black circles.

There may be various methods of obtaining the representative points of the divided areas.

For example, first, a distance between a first data point and the division center point is calculated, and the divided area including the first data point is obtained. Then, the coordinates of the data point and the calculated distance from the division center point are stored as the representative point candidate. Next, a distance between a second data point and the division center point is calculated, and the divided area including the second data point is obtained. If there is the representative point candidate in the divided area including the second data point, it is determined whether the distance between the second data point and the division center point is greater than the distance between the representative point candidate and the division center point. When determining that the distance between the second data point and the division center point is greater than the distance between the representative point candidate and the division center point, the coordinates of the second data point and the calculated distance from the division center point are stored as a new representative point candidate. When determining that the distance between the second data point and the division center point is less than the distance between the representative point candidate and the division center point, the information of the representative point candidate remains (without being changed). When determining that the distance between the second data point and the division center point is equal to the distance between the representative point candidate and the division center point, the coordinates of the second data point and the calculated distance from the division center point are stored as a new representative point candidate and the information of the previous representative point candidate remains without being changed. If there is no representative point candidate in the divided area including the second data point, the coordinates of the second data point and the calculated distance from the division center point are stored as the representative point candidate. After that, the above processes are performed on all the data points, so as to obtain the representative point candidates of the respective divided areas. After the processes on all the data points are completed, the representative point candidates are stored as the representative points of the respective divided areas.

However, the method of obtaining the representative points of the respective divided areas is not limited to the above method. For example, for the data points, the distances from the division center point are obtained, and, in each of the divided areas, the data point having the greatest distance from the division center point is selected as the representative point of the divided area. Further, for example, the data points are grouped based on the divided areas. Then, in each of the divided areas, the distances between the data points and the division center point are obtained. Then, the data point having the greatest distance from the division center point is selected as the representative point of the divided area.

In this case, it may be assumed that the divided area including no data points has no representative point, and the subsequent process may be performed based on this assumption. Further, in a case where the gravity center of the distribution area of the data points is set as the division center point, and the distribution area is evenly divided into four (4) divided areas in a manner such that the divided areas radiate from the division center point, and when there is the divided area including no data point, the coordinates of the division center point may be set as the representative point of the divided area including no data point.

Further, in the above description with reference to FIG. 3, a case is described where the number of the concentrated pattern defect distributions 9 is one. However, in step S4, when determining that plural concentrated pattern defect distributions 9 are detected for the pattern defect inspection data of the wafer information, the distribution representative point selection step of step S5 is performed on each of the plural concentrated pattern defect distributions 9.

Referring back to FIG. 1, the method in the flowchart of FIG. 1 is further described.

Step S6: It is determined whether there is an overlapping area 13 where a concentrated pattern defect distribution representative point area 11 overlaps the determination area 5, the concentrated pattern defect distribution representative point area 11 being formed by sequentially connecting the representative points of the concentrated pattern defect distribution 9 using lines. In this case, the concentrated pattern defect distribution representative point area 11 is defined by sequentially connecting sixteen (16) representative points with lines in a manner such that the lines are not crossed over each other. For example, such a concentrated pattern defect distribution representative point area 11 may be defined by connecting from the representative point as the start point to the next representing point of the adjacent area with a line and connecting in the same manner in clockwise or counterclockwise direction. In FIG. 6, a case is described where the lines between the representative points are straight lines. However, the present invention is not limited to this configuration. For example, by using the "DrawClosedCurve" method of Visual Basic (trade mark of Microsoft Corp.) or the like, the representative points of the concentrated pattern defect distribution representative point area 11 may be connected with smooth curves passing through the representative points. This alternative connecting method may also applied to the other embodiments described below.

As illustrated in FIG. 6, the concentrated pattern defect distribution representative point area 11 overlaps the determination area 5 forming the overlapping area 13. Therefore, it is determined that the concentrated pattern defect distribution 9 is determined to be the data group to be obtained (hereinafter may be referred to as a "relevant data group"). Further, the wafer information corresponding to the pattern defect inspection result data including the concentrated pattern defect distribution 9 is determined to be the wafer information having the pattern defect distribution to be obtained.

Further, in a case where, in step S4, it is determined that there are plural concentrated pattern defect distributions in one wafer information, and when, in step S5, the selection process of the representative points are selected for each of the concentrated pattern defect distributions, the distribution representative point area is defined for each of the concentrated pattern defect distributions, and it is determined whether there is the overlapped area where the distribution representative point area overlaps the determination area for each of the distribution representative point areas.

In this embodiment, the concentrated pattern defect distribution representative point area 11 is expressed by using four (4) representative points. Because of this feature, the information amount expressing the concentrated pattern defect distribution representative point area 11 is less than the information amount expressing the concentrated pattern defect distribution 9. Namely, in this embodiment, it can be determined whether the concentrated pattern defect distribution 9 is distributed in the specific determination area 5 while the information amount expressing the concentrated pattern defect distribution 9 is reduced by replacing the concentrated pattern defect distribution 9 with the concentrated pattern defect distribution representative point area 11.

In the embodiment described with reference to the flowchart of FIG. 1, whenever the determination step S6 is executed, the pattern defect data point group is formed (step S3), the concentrated pattern defect distribution is determined (step S4), and the representative points of the concentrated pattern defect distribution are selected (step S5).

However, when those processes are performed on the stored data and the processes are performed using the same references, it may be more reasonable to perform the representative point selection process on the data points (data group to be determined) when the data are collected, the data points being included in the concentrated pattern defect distribution, so that the representative point information is associated with the wafer information (identification information of data group to be determined) and stored in the database as the data. The embodiment is described with reference to FIG. 7.

Figure 7:
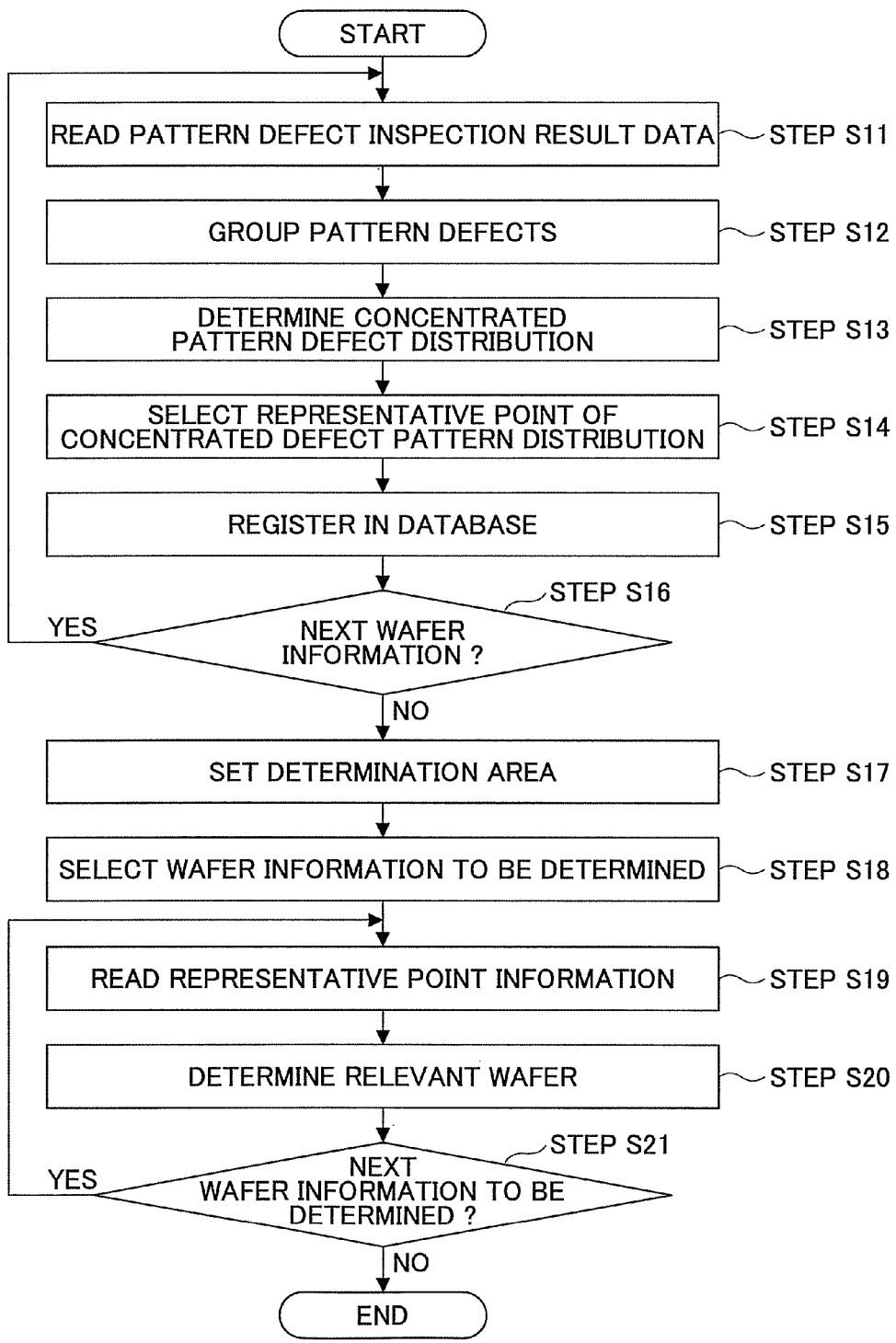
FIG. 7 is a flowchart illustrating a processing procedure of a method according to another embodiment of the present invention.

FIG. 7 is a flowchart illustrating a method according to another embodiment of the present invention. In this embodiment, the steps already described with reference to the flowchart of FIG. 1 may be described in a simple manner.

Steps S11 through S14: Similar to steps S2 through S5 of FIG. 1, the pattern defect inspection result data associated with the wafer information is read (step S11); the pattern defects are grouped (step S12); it is determined that the pattern defect is the concentrated pattern defect distribution (step S13); and the representative points of the concentrated pattern defect distribution are selected, the representative points representing the contour of the concentrated pattern defect distribution (step S14).

Step S15: the representative points information acquired in step S14 is associated with the wafer information and registered in the database. In this case, the distribution range of the concentrated pattern defect distribution and characteristic information may also be associated with the wafer information and registered in the database, the characteristic information including at least one of an area (size), a roundness rate, and a distribution density of the distribution representative point area defined by sequentially connecting the representative points with lines in a manner such that the lines are not crossed over each other. Further, there are various information to be associated with the wafer information, the various information including a lot number, a manufacturing method, a product type name, a process name, an inspection completion date, and the like for identifying the wafer. Further, when the wafer test is completed, as the wafer test result information, the information such as the determination test result (PASS or FAIL) of the chips, and the test category corresponding to the FAIL test result may also be associated with the wafer information.

Step S16: It is determined whether next wafer information exists. When determining that the next wafer information exists (YES in step 16), the process goes back to step S11 and the processes of steps S11 through S15 are performed on the next wafer information. When determining that there is no wafer information (NO in step 16), the process goes to step S17.

Step S17: The determination area is set on the coordinate plane.

Step S18: From among the wafer information registered in the database, the wafer information to be determined is selected as the wafer information to be determined. For example, the wafer information to be determined having the representative points of the concentrated pattern defect distribution located in the determination area set in step S17 is selected. Otherwise, if the characteristic information is associated and registered with the wafer information in step S15, the wafer information to be determined may be selected based on the characteristic information. Otherwise, the wafer information to be determined may be selected based on the information indicating the lot number, the product type name, the inspection execution date or the like.

Step S19: The representative point information of the wafer information selected in step S18 is read.

Step S20: Similar to step S6 of FIG. 1, it is determined whether there is the overlapping area where the concentrated pattern defect distribution area overlaps the determination area. When determining that there is the overlapping area, the concentrated pattern defect distribution area is determined to be the wafer information having the pattern defect inspection result data including the pattern defect distribution to be obtained.

Step S21: It is determined whether any of the wafer information to be determined selected in step S18 is remaining. When determining that any of the wafer information to be determined selected in step S18 is remaining (YES in step S21), the process goes back to step S19 to perform the processes of steps S19 and S20 on the next wafer information to be determined. When determining that none of the wafer information to be determined selected in step S18 is remaining (NO in step S21), the process ends.

In step S15, the representative points information may be associated with the wafer information to be determined and registered in database. By doing this, it may become possible to skip the distribution representative point selection step of steps S11 through S14 by reading the representative point information from the database to perform the wafer determination (in step S20). As a result, the processing time may be reduced.

Further, the information amount of the representative points of the concentrated pattern defect distribution is less than the information amount of all defect data points included in the concentrated pattern defect distribution 9. Therefore, it may become possible to reduce the reading time and the processing time.

In the above embodiments, in steps S6 and S20 where the wafer is determined, the determination may be made depending on whether the area of the concentrated pattern defect distribution representative point area 11 is equal to or greater than a predetermined defect distribution representative point area threshold value. In this case, in steps S6 and S20, when determining that the area of the concentrated pattern defect distribution representative point area 11 is less than a predetermined defect distribution representative point area threshold value, it may be determined that the concentrated pattern defect distribution representative point area 11 is not the wafer information to be determined (relevant wafer information). By doing this, it may become possible to remove the wafer information having the concentrated pattern defect distribution representative point area 11 having the size less than the size of the concentrated pattern defect distribution representative point area 11 of the wafer information to be obtained. Therefore, it may become possible to improve the determination accuracy of the wafer information to be obtained.

This determination process of the area of the distribution representative point area may be performed before or after the determination process of determining the existence of the overlapping area. When the determination process of the area of the distribution representative point area is performed before the determination process of determining the existence of the overlapping area, it may become possible not to perform the determination process of determining the existence of the overlapping area for the distribution representative point area that has a small area and that has to be removed.

Further, in steps 6 and 20 where the wafer is determined, it may be further determined whether the overlapping area 13 is equal to or greater than a predetermined overlapping area threshold value. In steps 6 and 20, when determining that the overlapping area 13 is equal to or greater than the predetermined overlapping area threshold value, it may be determined that the concentrated pattern defect distribution representative point area 11 is the wafer information to be determined (relevant wafer information). By doing this, it may become possible to improve the determination accuracy of the wafer information.

Further, in step 6 and 20 where the wafer is determined, it may be further determined whether a ratio of the area of the determination area 5 to the area of the overlapping area 13 is equal to or greater than a predetermined first ratio threshold value. In steps 6 and 20, when determining that the ratio is equal to or greater than the first ratio threshold value, it may be determined that the concentrated pattern defect distribution representative point area 11 is the wafer information to be determined (relevant wafer information). By doing this, it may become possible to improve the determination accuracy of the wafer information.

Figure 8:
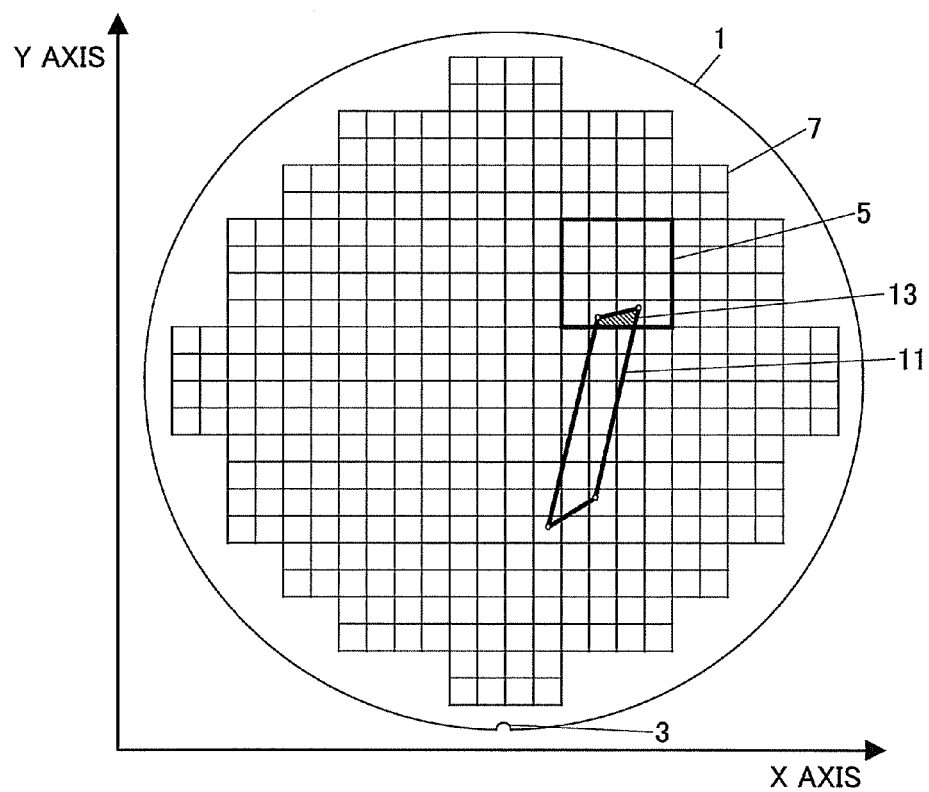
FIG. 8 is a drawing illustrating another example of the positional relationship between the determination area and the concentrated pattern defect distribution.

For example, as illustrated in FIG. 8, the determination area 5 overlaps the concentrated pattern defect distribution representative point area 11. However, when the ratio of the area of the determination area 5 to the area of the overlapping area 13 is less than, for example, 50%, it may be determined that the concentrated pattern defect distribution representative point area 11 is not the wafer information to be determined (relevant wafer information). By doing this, it may become possible to improve the determination accuracy of the wafer information.

Further, in steps 6 and 20 where the wafer is determined, it may be further determined whether a ratio of the area of the overlapping area 13 to the area of the concentrated pattern defect distribution representative point area 11 is equal to or greater than a predetermined second ratio threshold value. In steps 6 and 20, when determining that the ratio is equal to or greater than the second ratio threshold value, it may be determined that the concentrated pattern defect distribution representative point area 11 is the wafer information to be determined (relevant wafer information).

For example, as illustrated in FIG. 8, the determination area 5 overlaps the concentrated pattern defect distribution representative point area 11. However, when the ratio of the area of the overlapping area 13 to the area of the concentrated pattern defect distribution representative point area 11 is less than, for example, 50%, it may be determined that the concentrated pattern defect distribution representative point area 11 is not the wafer information to be determined (relevant wafer information). By doing this, it may become possible to improve the determination accuracy of the wafer information.

Further, in step 18 of FIG. 7, from among the wafer information to be determined registered in the database, when the wafer information that is to be determined is selected, it may become possible to reduce the processing time when compared with a case where all the wafer information to be determined registered in the database is processed. However, the present invention is not limited to this configuration. Namely, all the wafer information to be determined registered in the database may be read.

In step S18, when the wafer information to be determined is selected, the wafer information to be determined having the representative point of the concentrated pattern defect distribution located in the determination area set in step S17, the wafer information to be determined having a relationship between the determination area 5 and the representative points (white circles) as illustrated in FIG. 6 may be selected.

Figure 9:
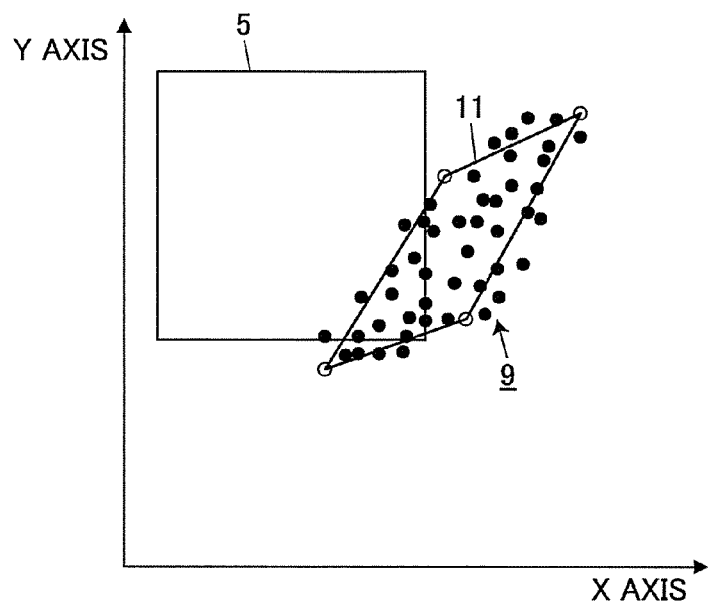
FIG. 9 is a drawing illustrating still another example of the positional relationship between the determination area and the concentrated pattern defect distribution.

However, depending on the disposed position of the determination area 5, for example, as illustrated in FIG. 9, there may be a case where the pattern defect data points (black circles) are disposed in the determination area 5, but not any of the representative points (while circles) is disposed in the determination area 5. In the case of the positional relationship between the determination area 5 and the representative points as illustrated in FIG. 9, the wafer information to be determined having the representative points may not be selected in step S18.

If this is not desirable, in step S15, it may be possible to associate and register the characteristic information including the distribution range of the concentrated defect distribution and at least one of the area of the distributed representative area, the roundness rate, and the data point distribution density with the wafer information to be determined. Further, in step S18, the wafer information to be determined may be selected based on the characteristic information. Specific examples of the characteristic information are described below.

For example, the wafer information to be determined is associated with the distribution range of the concentrated defect distribution.

Figure 10:
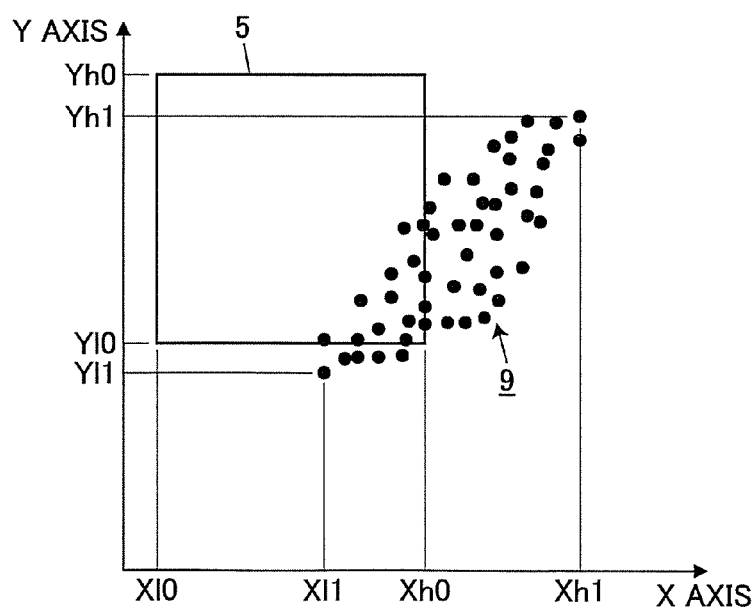
FIG. 10 is a drawing illustrating an example of a distribution range display of the concentrated pattern defect distribution.

FIG. 10 illustrates one example of the distribution range of the concentrated defect distribution. From among the XY coordinate values of all the data points included in the concentrated pattern defect distribution, the information expressing the distribution range of the concentrated pattern defect distribution 9 is expressed by using the four values: the maximum value Xh1 and the minimum value Xl1 of the X axis and the maximum value Yh1 and the minimum value Yl1 of the Y axis. On the other hand, the range of the determination area 5 is expressed by the four values: the maximum value Xh0 and the minimum value Xl0 of the X axis and the maximum value Yh0 and the minimum value Yl0 of the Y axis.

In this case, the search conditions for making a short list of (narrow down, reducing the number of candidates (options)) the wafer information to be determined are: Xh1>Xl0, Xl1<Xho, Yh1>Yl0, and Yl1<Yho.

By setting the conditions in this way, it may become possible to select wafer information having the concentrated pattern defect distribution 9 illustrated in FIG. 10.

In this case, the four (4) values, that is the maximum value Xh1 and the minimum value Xl1 of the X axis and the maximum value Yh1 and the minimum value Yl1 of the Y axis, are obtained by using all the data points included in the concentrated pattern defect distribution 9. However, alternatively, those maximum and minimum values may be obtained using only the representative points as the information expressing the distribution range of the concentrated pattern defect distribution 9.

Figure 11:
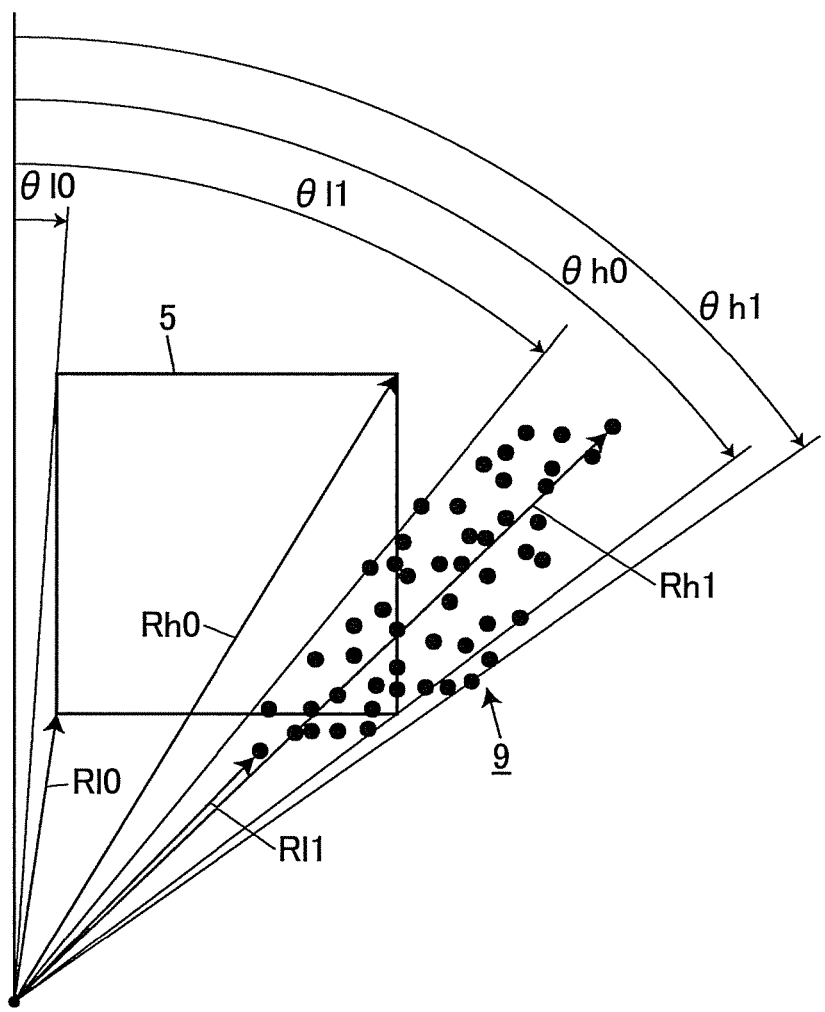
FIG. 11 is a drawing illustrating another example of a distribution range display of the concentrated pattern defect distribution.

FIG. 11 illustrates another example of the distribution range of the concentrated pattern defect distribution 9.

In FIG. 10, the XY coordinate system is used.

However, the polar coordinate system may alternatively be used to express the distribution range of the concentrated pattern defect distribution 9.

When the polar coordinate system is used, from among the "R" values and "θ" values of all the data points included in the concentrated pattern defect distribution 9, the information expressing the distribution range of the concentrated pattern defect distribution 9 is expressed by the four values: the maximum value Rh1 and the minimum value Rl1 of the R values and the maximum value θh1 and the minimum value θl1 of the θ values. On the other hand, the range of the determination area 5 is expressed by the four values: the maximum value Rh0 and the minimum value Rl0 of the R values and the maximum value θh0 and the minimum value θl0 of the θ values.

In this case, the search conditions for making a short list of (narrow down) the wafer information to be determined are: Rh1>Rl0, Rl1<Rho, θh1>θl0, and θl1<θho.

By setting the conditions in this way, it may become possible to select wafer information having the concentrated pattern defect distribution 9 illustrated in FIG. 11.

In this case, the four values, that is the maximum value Rh1 and the minimum value Rl1 of the R values and the maximum value Oh1 and the minimum value θl1 of the θ values, are obtained by using all the data points included in the concentrated pattern defect distribution 9. However, alternatively, those maximum and minimum values may be obtained using only the representative points as the information expressing the distribution range of the concentrated pattern defect distribution 9.

Further, the area of the concentrated pattern defect distribution representative point area 11 is one of the information expressing the feature of the concentrated pattern defect distribution 9. Therefore, by using the representative points selected in step S14, the area of the concentrated pattern defect distribution representative point area 11 is obtained (see FIG. 12). Then, in step S15, the area information is associated with the wafer information and registered in the database. Then, in step S18, the wafer information to be determined is selected based on the area of the concentrated pattern defect distribution representative point area 11. By doing in this way, in step S20 where the wafer information is determined, it may become possible to omit the determination process that the concentrated pattern defect distribution representative point area 11 having an area less than a threshold value is not the wafer information to be determined.

Further, the information expressing the feature of the shape of the concentrated pattern defect distribution representative point area 11 may be obtained and registered, so that the information is used for selecting the wafer information to be determined. For example, as a value expressing to what extent the shape of the concentrated pattern defect distribution representative point area 11 is similar to a circle, a value obtained by dividing the area of the concentrated pattern defect distribution representative point area 11 by the area of a circle having a circumference equal to a line length surrounding the concentrated pattern defect distribution representative point area 11 is obtained, and the value (hereinafter "roundness rate") is associated with the wafer information and registered in the database.

In this case, when line length surrounding the concentrated pattern defect distribution representative point area 11 is given as "L", the radius "r" of a circle having the circumference equal to "L" is given as "$L/2\pi$". Further, the area of the circle having the circumference equal to "L" is given as "$\pi r^2 = \pi(L/2\pi)^2 = L^2/4\pi$". When assuming that the area of the concentrated pattern defect distribution representative point area 11 is given as "S", the "roundness rate" is expressed as $S/(L^2/4\pi) = 4\pi S/L^2$.

When the roundness rate approaches 1, the shape approaches a circle, and when the roundness rate approaches 0, the shape approaches a line. Therefore, by using this feature, the "roundness rate" may be used when the wafer information to be determined in the distribution identification target wafer selection step on as needed basis.

Further, the number of pattern defect data points in the concentrated pattern defect distribution representative point area 11, that is the distribution density may be one of the information expressing the feature of the concentrated pattern defect distribution.

Figure 12:
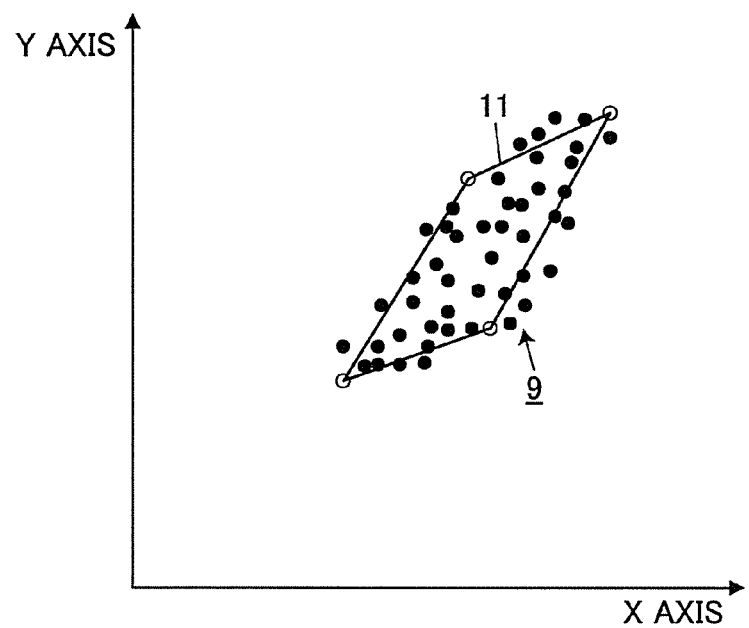
FIG. 12 is a drawing illustrating an example of a data point distribution density in the concentrated pattern defect distribution.
Figure 13:
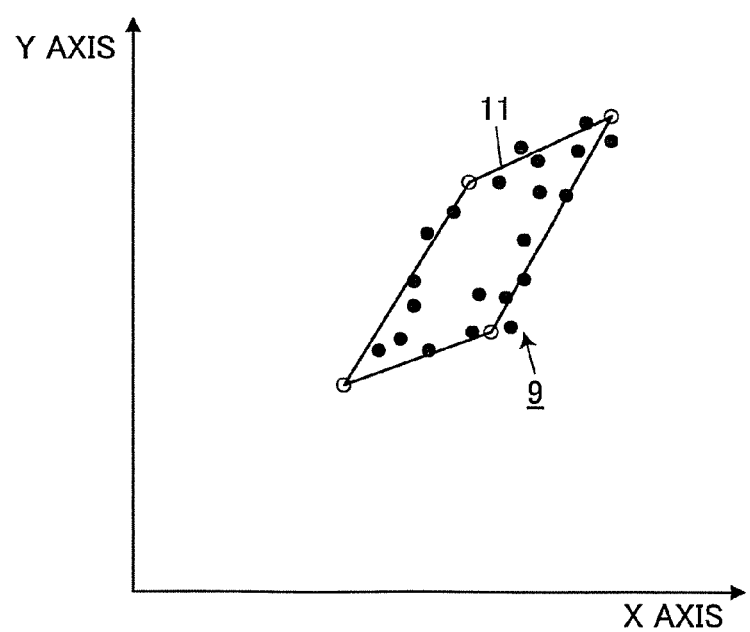
FIG. 13 is a drawing illustrating another example of a data point distribution density in the concentrated pattern defect distribution.

When the concentrated pattern defect distribution representative point area 11 of the concentrated pattern defect distribution 9 in FIG. 12 is compared with the concentrated pattern defect distribution representative point area 11 of the concentrated pattern defect distribution 9 in FIG. 13, the sizes of the concentrated pattern defect distribution representative point areas 11 are the same as each other; however, the numbers of the pattern defect data points differ from each other. Namely, the density of the pattern defect data points in FIG. 12 is higher than the density of the pattern defect data points in FIG. 13. Therefore, the data point distribution density of the data point distribution area of the concentrated pattern defect distribution representative point areas 11 may be obtained in advance, associated with the wafer information, and registered in the database. By doing this, it may become possible to exclude (remove) the concentrated pattern defect distribution 9 having a lower data point distribution density of the data point distribution area of the concentrated pattern defect distribution 9 as illustrated in FIG. 13 and select only the concentrated pattern defect distribution 9 having a higher data point distribution density of the data point distribution area of the concentrated pattern defect distribution 9 as illustrated in FIG. 12, so that this feature can be utilized in selecting the wafer information to be determined.

In the above embodiment, the data points indicating the pattern defect position are used.

However, by using the data points indicating the particle positions (of foreign matters) based on the particle (contamination) inspection result, the processes similar to the processes in the above embodiment may be performed.

Further, the chip positions corresponding to data point positions indicating the pattern defect positions and particle positions may be regarded as the positions of defective chips. Then, by using the data indicating the defective chip positions, the processes similar to the processes in the above embodiment may be performed. However, there may be no concept of chips in the particle (contamination) inspection result data for a mirror surface wafer. In this case, "virtual" chips may be set on the wafer.

Figure 14:
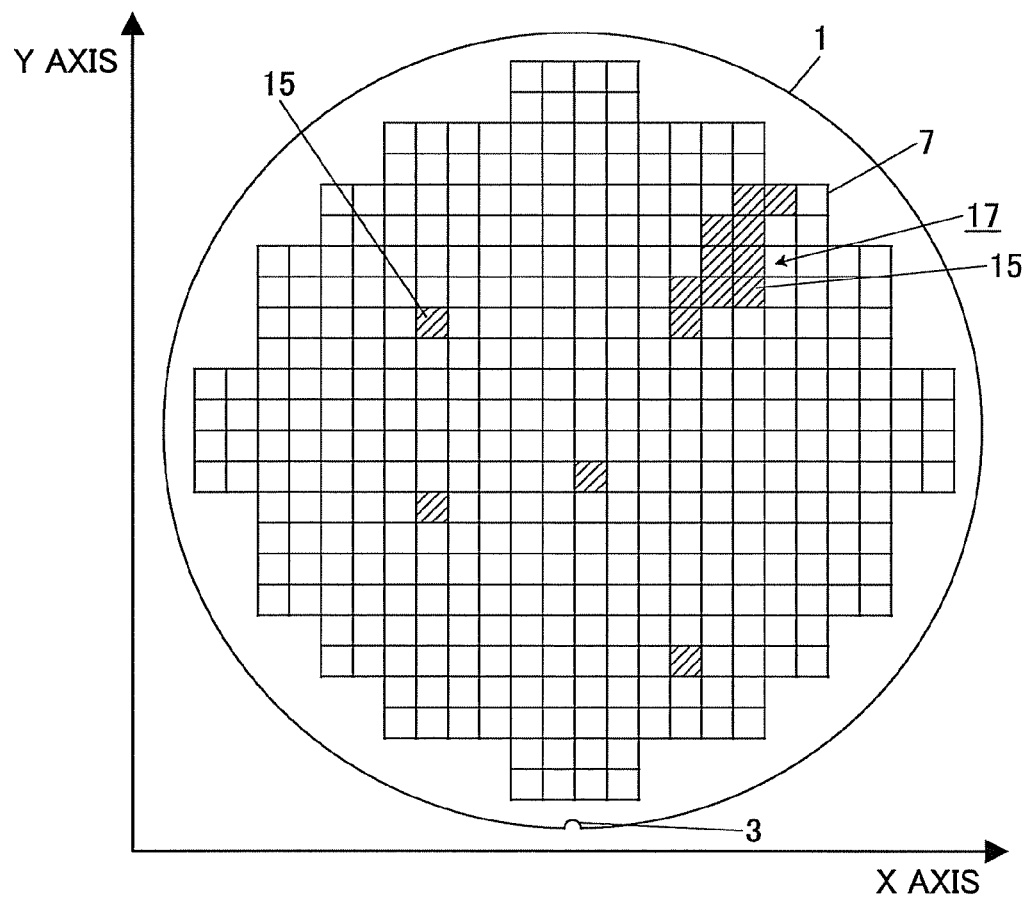
FIG. 14 is a drawing in which the pattern defect positions in FIG. 3 are replaced by defective chips.

For example, FIG. 14 illustrates a case where the pattern defect positions on the wafer of FIG. 3 are replaced by the defective chip positions. In FIG. 14, the defective chips are denoted by the reference numeral 15.

Similar to step S3 described with reference to FIG. 1, the defective chips 15 are grouped in a manner such that the defective chips 15 having the mutual distance less than a predetermined threshold value are determined to be included in the same group. However, a method of grouping the defective chips 15 is not limited to this method, and any other appropriate method may alternatively used. For example, the defective chips 15 may be grouped based on a method disclosed in Japanese Patent Application Publication No. 2009-10303.

Similar to step S4 described with reference to FIG. 1, for each of the groups of the defective chips 15, it is determined whether the group is the concentrated pattern distribution when the number of the defective chips 15 is five (5) or more. In the case of FIG. 14, the defective chip group 17 is determined to be the concentrated defect distribution.

Figure 15:
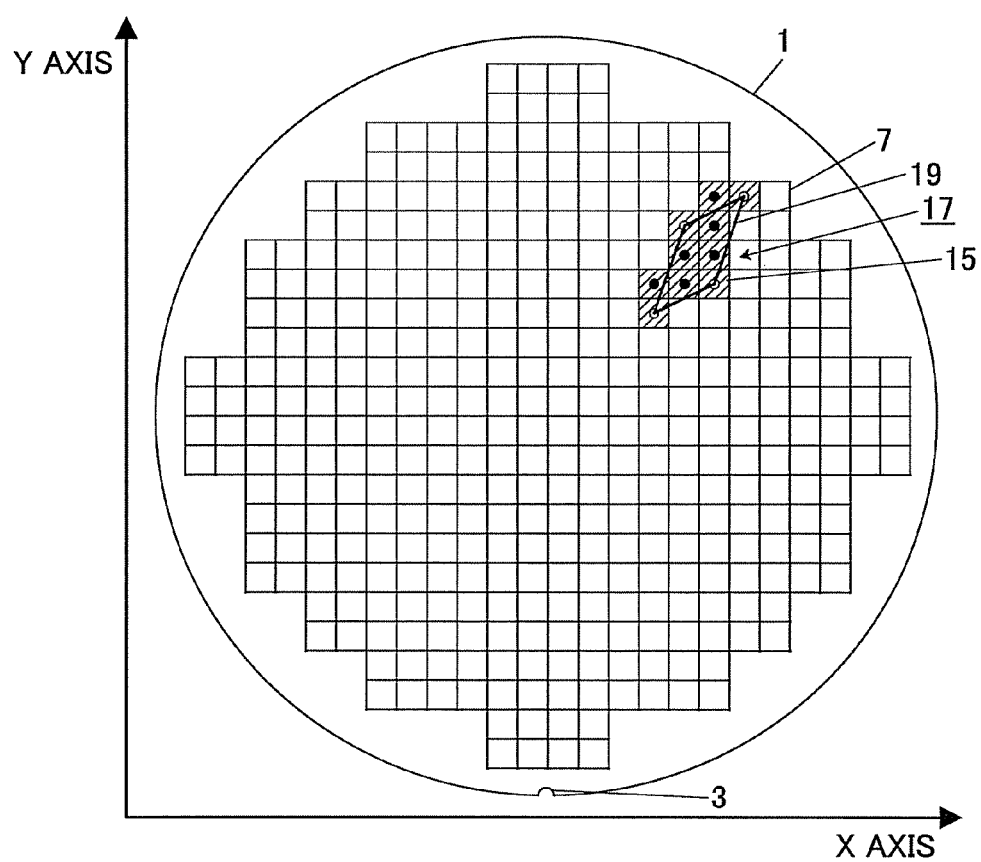
FIG. 15 is a drawing illustrating representative points of a concentrated defect distribution and a representative point distribution area.

Chip positional information refers to the information indicating the positions of the chips 7 on the wafer 1. Therefore, for example, the chip positional information may be replaced by the positional information expressing the center points of the chips 7. By using the positional information expressing the center points of the defective chips 15, the processes similar to the processes of step S5 described with reference to FIG. 1 and steps S5-1 through S5-3 described with reference to FIG. 4 are performed. As a result, as illustrated in FIG. 15, the representative points (white circles) of the concentrated defect distribution 17 are obtained. In FIG. 15, the black circles and the white circles denote the center points of the defective chips 15 of the concentrated defect distribution 17. FIG. 15 further illustrates a concentrated defect distribution representative point area 19 that is formed by sequentially connecting the representative points of the concentrated defect distribution 17 with lines.

After that, similar to step S6 described with reference to FIG. 1, it is determined whether the concentrated defect distribution representative point area 19 is the wafer information to be determined based on whether there is the overlapping area where the concentrated defect distribution representative point area 19 overlaps the determination area.

In FIG. 14, as described above, the chip positional information is replaced by the positional information expressing the center points of the chips 7. On the other hand, the wafer test result data include chip positional information and the test results (PASS or FAIL) of the chips. Therefore, the processes similar to the processes described with reference to FIGS. 14 and 15 may also be performed on the wafer test result data.

Figure 16:
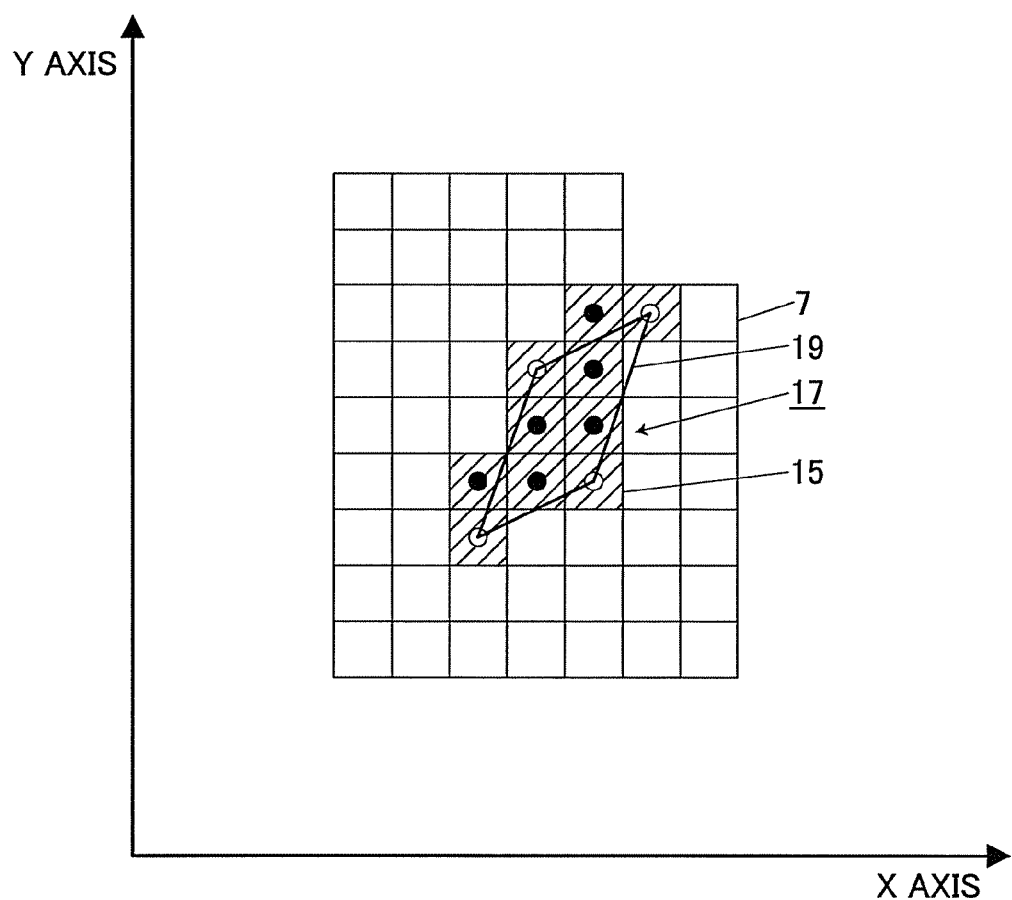
FIG. 16 is an enlarged view of the vicinity of the concentrated defect distribution in FIG. 15.

FIG. 16 is an enlarged view of the vicinity of the concentrated defect distribution 17 of FIG. 15.

In this case, when the concentrated defect distribution representative point area 19 corresponding to the concentrated defect distribution 17 is to be obtained by obtaining the representative points (white circles) using the center points (black circles and white circles) of the centers of the chips 7 and the defective chips 15, a large part of the area of the defective chips 15 of the concentrated defect distribution 17 protrudes from the area of the concentrated defect distribution representative point area 19.

When this is not desirable, the positional information indicating the chips 7 of the wafer test result data is replaced by the positional information indicating the four corners of the chips 7 and then the representative points of the concentrated defect distribution 17 are obtained.

Figure 17:
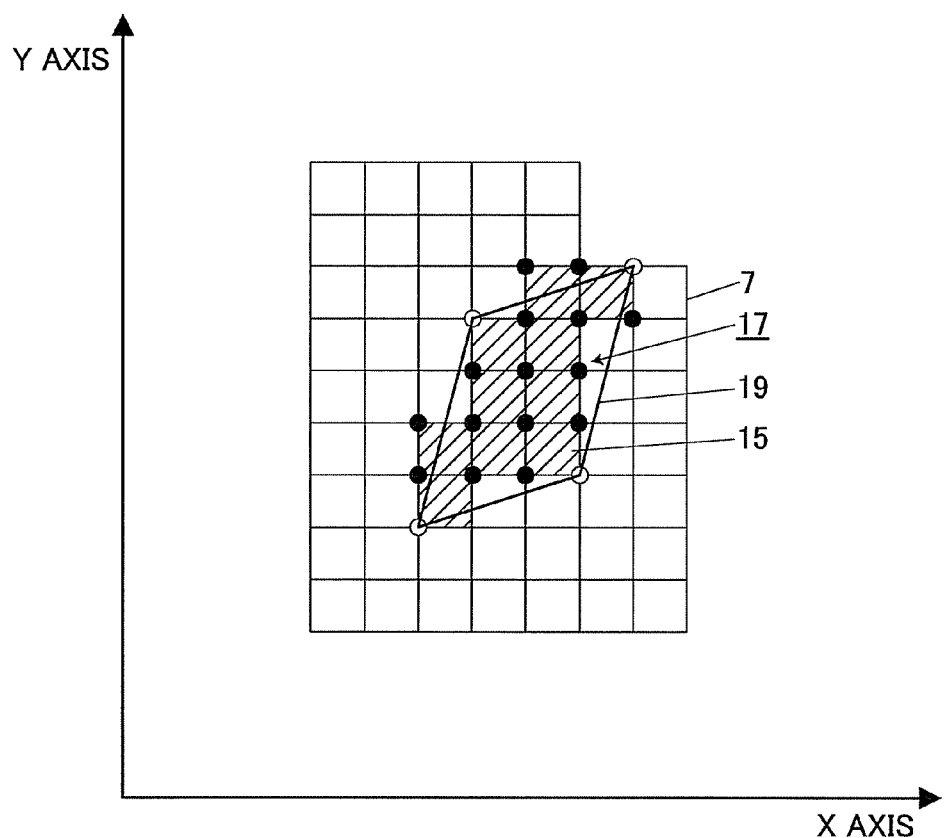
FIG. 17 is a drawing illustrating the representative points and the concentrated defect distribution representative point area when the positional information in FIG. 16 is replaced by the four (4) corners of the chips.

FIG. 17 illustrates the representing points and the concentrated defect distribution representative point area 19 when the positional information indicating the chips 7 of the wafer test result data in FIG. 16 is replaced by the positional information indicating the four corners of the chips 7.

As illustrated in FIG. 17, when the concentrated defect distribution representative point area 19 corresponding to the concentrated defect distribution 17 is obtained by obtaining the representative points (white circles) using the positional information (black circles and white circles) indicating the four (4) corners of the defective chips 15, the part of the area of the defective chips 15 of the concentrated defect distribution 17 that protrudes from the area of the concentrated defect distribution representative point area 19 becomes smaller.

In the above embodiment, as illustrated in, for example, FIG. 2, the determination area 5 is set on a part of upper right-hand side when the wafer 1 is set in a manner such that the notch 3 of the wafer 1 is arranged on the lower side. However, the determination area 5 may be set at any position and area.

For example, the determination area 5 may be set as the upper half part or the right half part of the wafer 1 assuming the notch 3 is arranged on the lower (bottom) side.

Further, it is not always necessary that the determination area 5 has a frame shape. For example, the determination area 5 may have a shape other than the frame shape and may be expressed as an area defined by X>0 and Y>0 or an area defined by X<2 in the XY coordinate plane.

Figure 18:
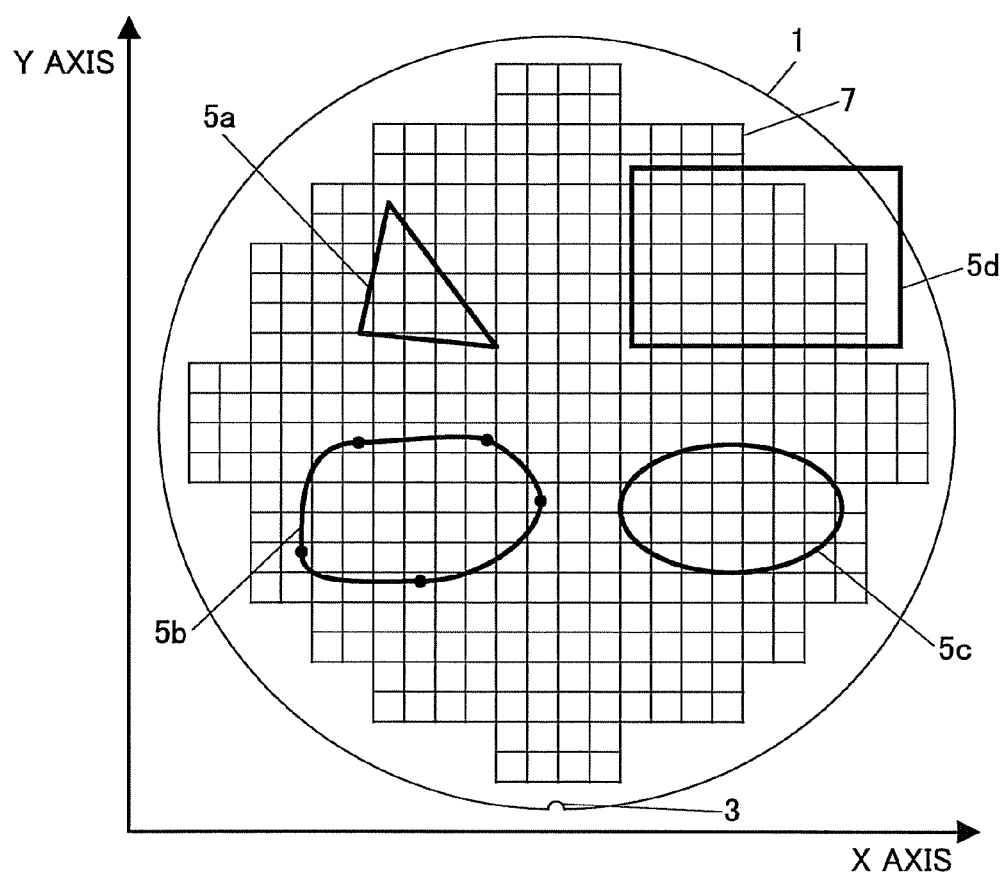
FIG. 18 is a drawing illustrating examples of the determination areas.
Figure 19:
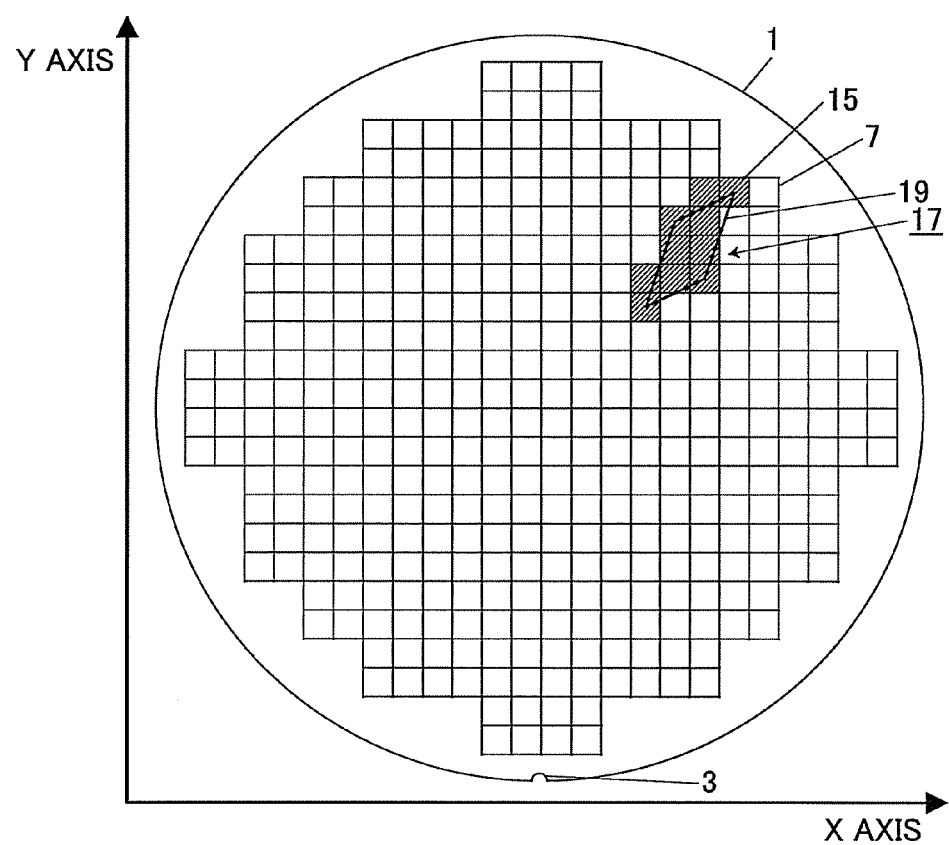
FIG. 19 is a drawing illustrating a wafer test result on a coordinate plane.

FIG. 18 illustrates some examples of the determination area 5. As illustrated in FIG. 19, the determination area 5 may be a determination area 5a having a triangular shape, a determination area 5b formed by connecting the plural points with smooth curves, a determination area 5c having an elliptic shape, or a determination area 5d including an area protruding from the wafer 1 or the like.

Next, a specific use according to an embodiment of the present invention is described with reference to FIGS. 19 through 23.

FIG. 19 illustrates the wafer test result data on the coordinate plane. Specifically, FIG. 19 illustrates the concentrated defect distribution 17 and the concentrated defect distribution representative point area 19 corresponding to the concentrated defect distribution 17, the concentrated defect distribution 17 including the plural defective chips 15.

Figure 20:
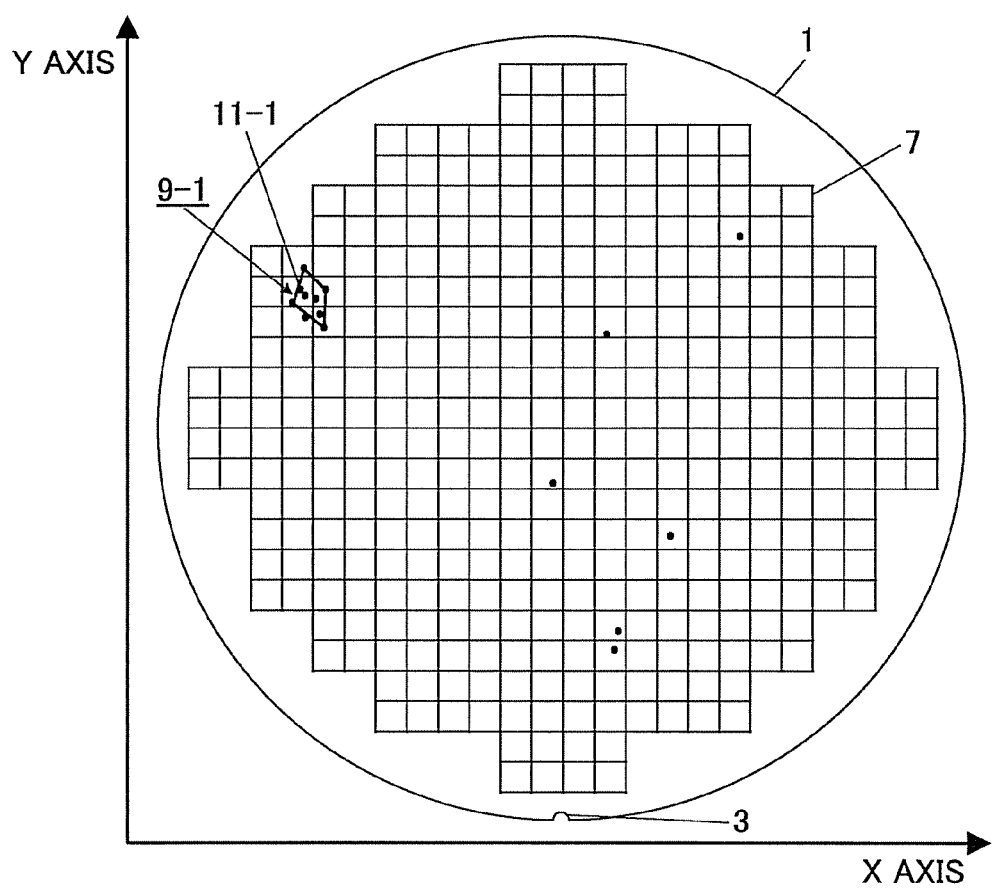
FIG. 20 is a drawing illustrating a defect inspection result of a metal 1 forming process on the coordinate plane.

FIG. 20 illustrates the defect inspection result data of a metal 1 forming process on the coordinate plane. Specifically, FIG. 20 illustrates data points (black circles) indicating the pattern defect positions, the concentrated pattern defect distribution 9-1, and the concentrated pattern defect distribution representative point area 11-1 corresponding to the concentrated pattern defect distribution 9-1.

Figure 21:
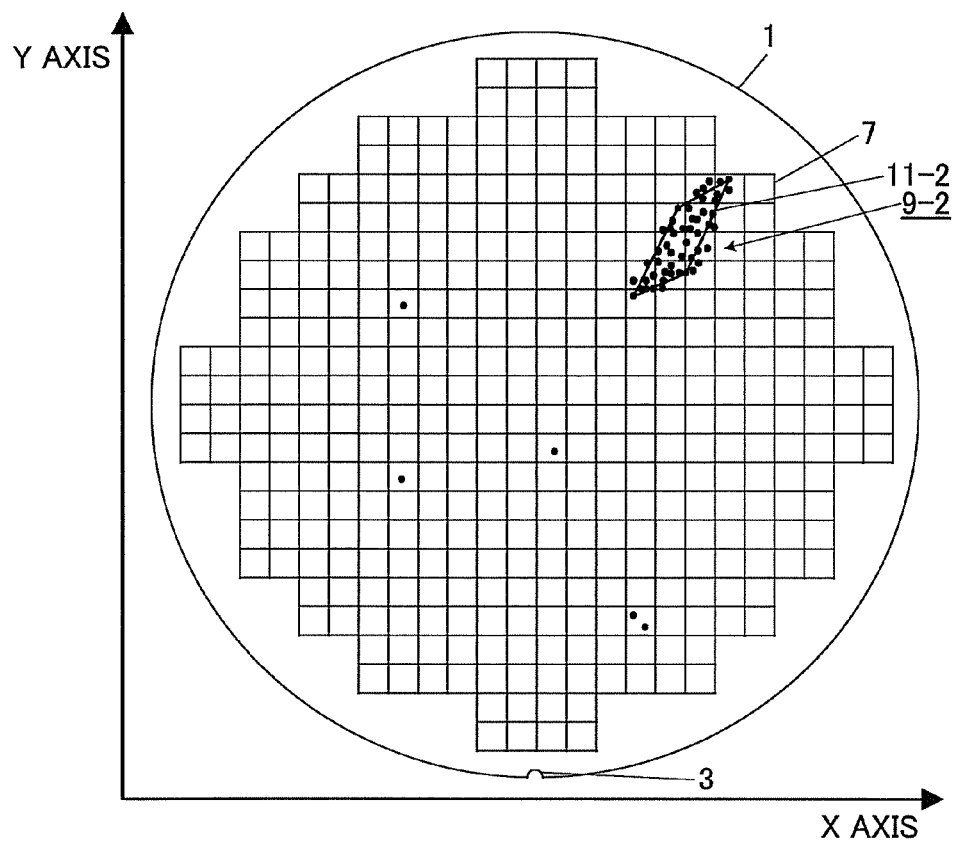
FIG. 21 is a drawing illustrating a defect inspection result of a metal 2 forming process on the coordinate plane.

FIG. 21 illustrates the defect inspection result data of a metal 2 forming process on the coordinate plane. Specifically, FIG. 21 illustrates data points (black circles) indicating the pattern defect positions, the concentrated pattern defect distribution 9-2, and the concentrated pattern defect distribution representative point area 11-2 corresponding to the concentrated pattern defect distribution 9-2.

Figure 22:
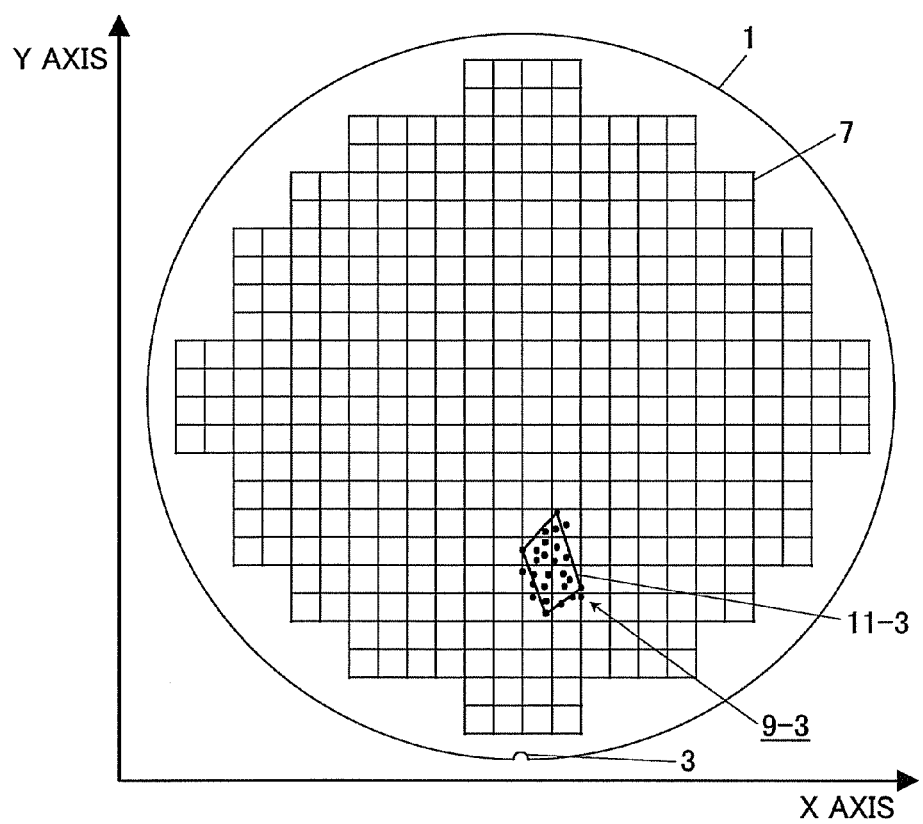
FIG. 22 is a drawing illustrating a defect inspection result of a metal 3 forming process on the coordinate plane.

FIG. 22 illustrates the defect inspection result data of a metal 3 forming process on the coordinate plane. Specifically, FIG. 22 illustrates data points (black circles) indicating the pattern defect positions, the concentrated pattern defect distribution 9-3, and the concentrated pattern defect distribution representative point area 11-3 corresponding to the concentrated pattern defect distribution 9-3.

Figure 23:
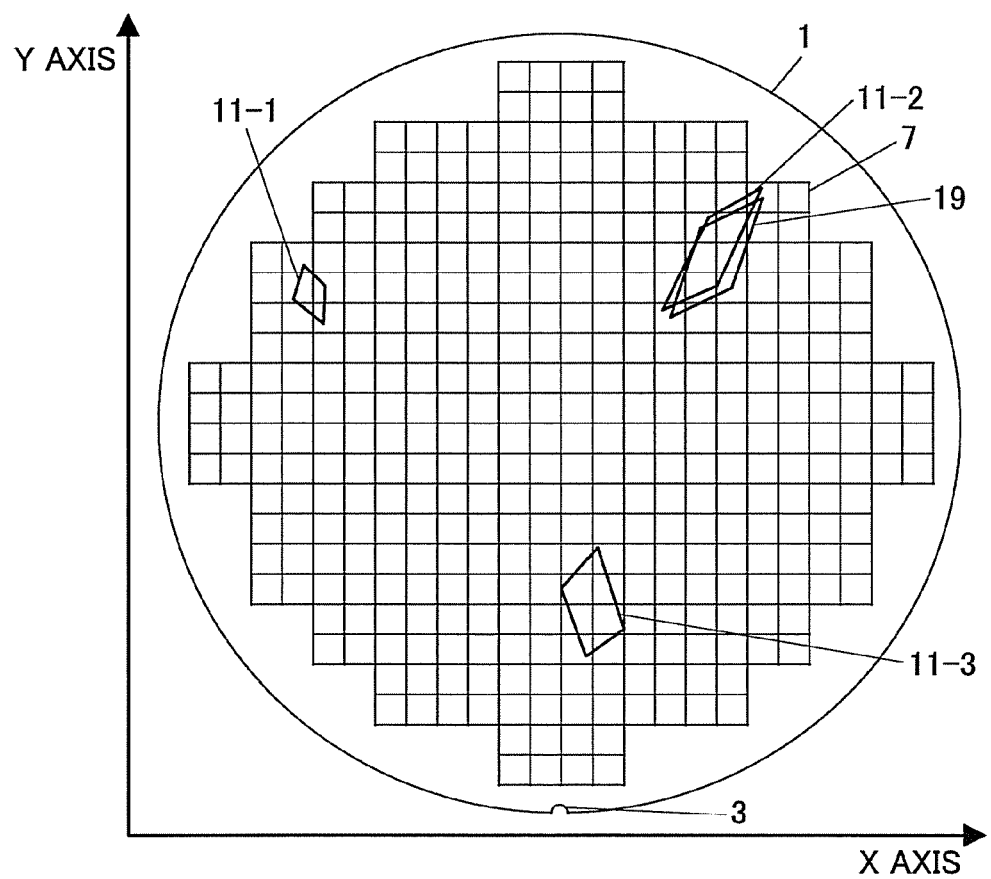
FIG. 23 is a drawing illustrating the concentrated pattern defect distribution representative point areas and the concentrated defective distribution representative point area of FIGS. 19, 20, 21, and 22 in a manner such that the areas are overlapped with each other.

In FIG. 23, the concentrated defect distribution representative point area 19 and the concentrated pattern defect distribution representative point areas 11-1, 11-2 and 11-3 of FIGS. 19, 20, 21, and 22, respectively, are illustrated in an overlapped manner.

In the wafer test result, when the concentrated defect distribution 17 as illustrated in FIG. 19 is obtained, by setting the concentrated defect distribution representative point area 19 corresponding to the concentrated defect distribution 17 as the determination area, it may be determined that the concentrated pattern defect distribution representative point area is the wafer information to be determined for each of the pattern defect inspection results of the metal forming processes. When the pattern defect inspection result of the metal forming processes is defective, the defective pattern defect inspection result includes the concentrated pattern defect distribution representative point area overlapping the concentrated defect distribution representative point area 19 (determination area 5) as the concentrated pattern defect distribution representative point area 11-2 of the metal 2 forming process. By using this feature, it may become possible to select the wafer information to be determined which includes the information indicating the cause of the occurrence of the concentrated defect distribution 17.

The steps of the embodiment described above may be realized by executing a program using a computer, the program being generated for the execution of the steps described above.

Further, as a function of the program, it may be preferable to draw the distributed defect distribution representative point areas or the concentrated pattern defect distribution representative point areas of the plural wafer information having been determined as the wafer information on one coordinate plane, and allow selecting unnecessary distributed defect distribution representative point areas or the concentrated pattern defect distribution representative point areas so as to remove those wafer information from all the wafer information. By having this function, it may become possible to adequately select the wafer information.

Figure 24:
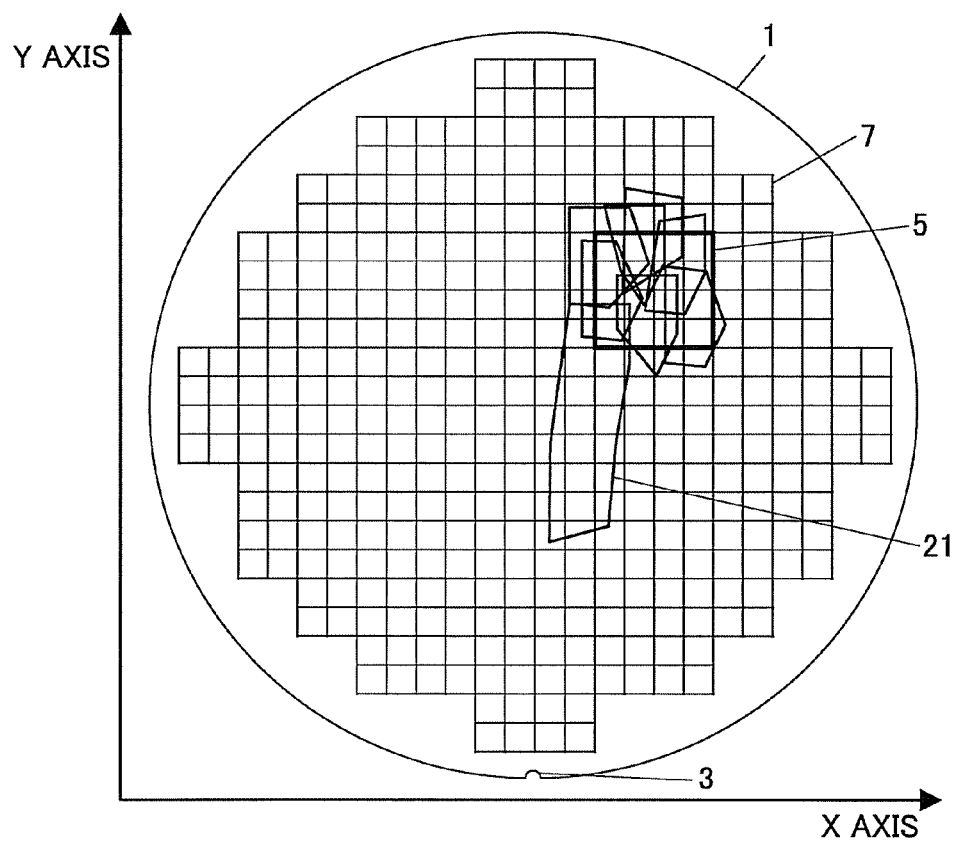
FIG. 24 is a drawing illustrating the concentrated pattern defective distribution representative point areas and the determination area on one coordinate plane, the concentrated pattern defective distribution representative point areas corresponding to the concentrated pattern defect distributions of plural wafer information.

Namely, as illustrated in FIG. 24, when it is desirable to remove the wafer information having the concentrated pattern defect distribution corresponding the concentrated pattern defect distribution representative point area having the distribution in an area far from the determination area 5, like the concentrated pattern defect distribution representative point area 21 in FIG. 24, from the wafer information, it may be preferable to display a figure illustrating the concentrated pattern defect distribution representative point areas of the plural wafer information on one coordinate plane, and allow selecting peculiar concentrated pattern defect distribution representative point area using a mouse or the like so as to remove the wafer information having the concentrated pattern defect distribution corresponding to the selected peculiar concentrated pattern defect distribution representative point area. Further, when the first ratio threshold value and the second ratio threshold value described with reference to FIG. 8 are used, it may become possible to automatically remove the wafer information corresponding to the concentrated pattern defect distribution representative point area 21 in FIG. 24.

Next, a modified example in step of selecting the representative points is described.

Figure 25:
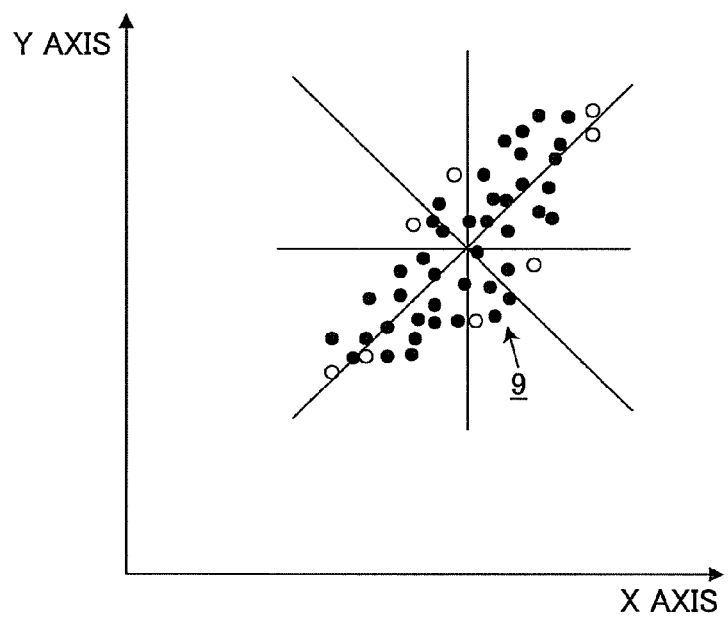
FIG. 25 is a drawing illustrating lines on the coordinate plane on which the concentrated pattern defect distribution illustrated in FIG. 5, so that the area of the coordinate plane is divided into eight (8) divided areas.
Figure 26:
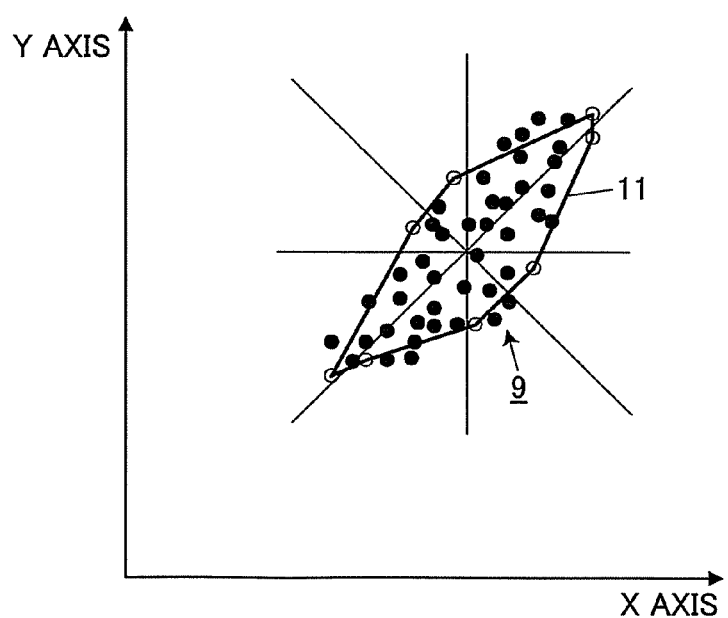
FIG. 26 is a drawing illustrating the concentrated pattern defect distribution representative point area of the concentrated pattern defect distribution on the coordinate plane of FIG. 25.

FIG. 25 illustrates the concentrated pattern defect distribution 9 of FIG. 5 and second dividing straight lines extending along the X axis direction so as to divide the area into eight (8) areas on the coordinate plane. FIG. 26 illustrates the concentrated pattern defect distribution representative point areas 11 of the concentrated pattern defect distribution 9 added to the coordinate plane of FIG. 25.

With reference to FIGS. 4, 25, and 26, the modified example of steps of selecting the representative points is described.

Similar to step S5-1 described with reference to FIG. 4, the division center point to divide the pattern defect distribution area into divided areas is set.

In step S5-2, the pattern defect distribution area is divided into eight (8) divided areas in a manner such that the divided areas radiate from the division center point. Herein, as the lines for dividing the pattern defect distribution area, a line that passes through the division center point and that is parallel to the X axis direction, a line that passes through the division center point and that is parallel to the Y axis direction, and lines that pass through the division center point and that are inclined +/−45 degrees with respect to the x axis are used, as illustrated as FIG. 25.

In step S5-3, in each of the divided areas, the data point having the greatest distance from the division center point is obtained (selected) as the representative point of the divided area. In FIG. 25, the data points of the representative points are displayed in white circles, and the data points other than the representative points are displayed in black circles.

As determination steps S6 and S20 illustrated in FIGS. 1 and 7, respectively, for the concentrated pattern defect distribution 9 and the representative points illustrated in FIG. 25, the concentrated pattern defect distribution representative point area 11 illustrated in FIG. 26 is defined by connecting from the representative point as the start point to the next representing point of the adjacent area with a line and further connecting in the same manner in clockwise or counterclockwise direction.

When the angle between the lines for dividing the area is large, depending on the distribution state of the data points, the data distribution may not be sufficiently expressed by executing the above steps alone.

Figure 27:
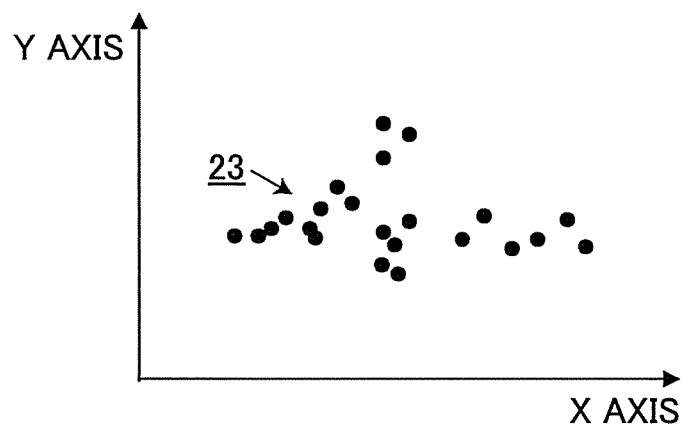
FIG. 27 is a drawing illustrating another example of the data point distribution state on the coordinate plane.
Figure 28:
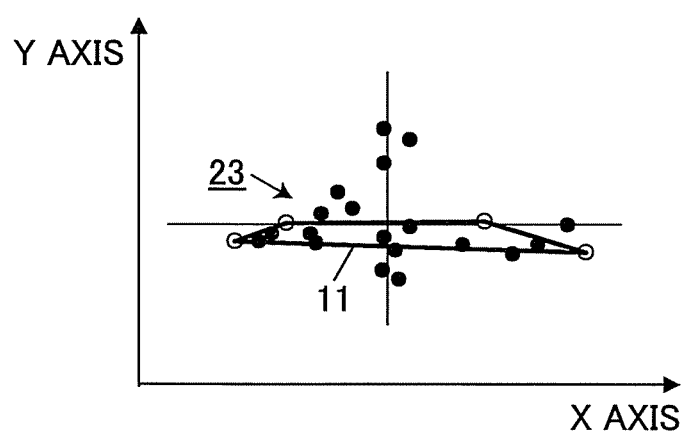
FIG. 28 is a drawing illustrating the representative points and the distribution representative point areas obtained by dividing the data point distribution of FIG. 27 into four (4) divided areas.

For example, there may be a distribution state of the data distribution as illustrated in FIG. 27. FIG. 28 illustrates the concentrated pattern defect distribution representative point area 11 obtained by setting the gravity center of the data distribution of FIG. 27 as the division center point, dividing the area into four (4) divided areas in a manner such that the divided areas radiate from the division center point, obtaining the representative points of the respective divided areas, and connecting the representative points.

In FIG. 28, white circles represent the representative points of the divided areas. In this case, as illustrated in FIG. 28, there is a data point much separated from the concentrated pattern defect distribution representative point area 11.

Figure 29:
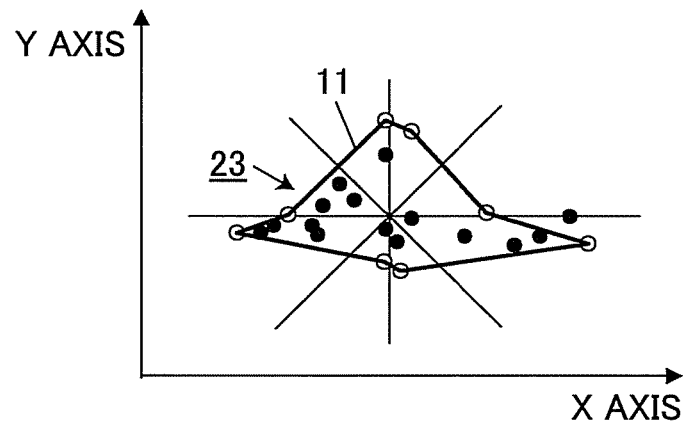
FIG. 29 is a drawing illustrating the representative points and the distribution representative point areas obtained by dividing the data point distribution of FIG. 27 into eight (8) divided areas.

To resolve this problem, there may be a method in which the angle between the lines defining the divided areas is narrower. In other words, the number of the divided areas is increased. For example, the distribution area may be divided into eight (8) divided areas. When this method is applied, for example, the distribution area is divided into eight (8) divided areas by narrowing the angle between the lines for defining the divided areas when compared with a case of FIG. 28. In this cased of FIG. 29, white circles represent the representative points of the respective divided areas. When the defined concentrated pattern defect distribution representative point area 11 in FIG. 29 is compared with that in FIG. 28, the concentrated pattern defect distribution representative point area 11 in FIG. 29 is defined more appropriately.

Further, to resolve the above problem, there may be a method in which a representative point necessary for defining an appropriate concentrated pattern defect distribution representative point area 11 is added. The method of obtaining the representative point to be added is described.

Two (2) divided areas adjoining each other are defined as a consideration area. When the representative point to be added is to be obtained, vectors from the division center point to the positions of the data points are used. The magnitude (length) of the component of the vector in the direction parallel to the extending direction of the line that is between the two divided areas of the consideration area and that passes through the division center point is used (compared) as an index. In the consideration area, from among the data points having the magnitude of the component of the vector greater than the magnitude of the component of any of the representative points, the data point having the greatest magnitude of the component of the vector is selected as the representative point to be added. If there are two or more data points that meet the above condition within the consideration area, the data point having coordinate closest to the division center point is selected as the representative point to be added.

As the method of obtaining the magnitude of the component of the vector, for example, there is a method in which a line is provided, the line being orthogonal to the line between the two divided areas of the consideration area and passing through the division center point. This line is herein called a "consideration line". In this method, the shortest length between the data point and the consideration line denotes the magnitude of the component. However, the method of obtaining the magnitude of the component is not limited to this.

Further, among the representative points in the consideration area, the representative point having the greatest magnitude of the component may be used and called a comparative representative point. In this case, from among the data points having the magnitude of the component greater than that of the comparative representative point, the data point having the greatest magnitude of the component is added as the representative point.

Figure 30:
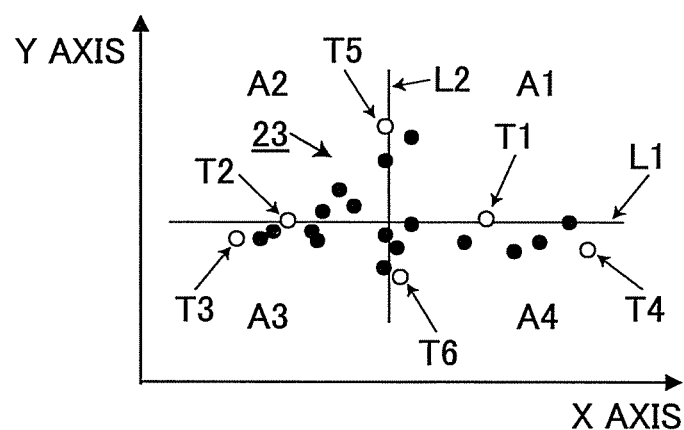
FIG. 30 is a drawing illustrating a method of obtaining the representative points to be added to represent the distribution area of the data point distribution of FIG. 27.

With reference to FIG. 30, a method of obtaining the representative point to be added to express a data point distribution 23 using the consideration line and the comparative representative point is described.

In FIG. 30, there are four (4) divided areas A1 through A4, and the representative points of the divided areas A1 through A4 are expressed as T1 though T4, respectively.

First, a case is described where the divided areas A1 and A2 in FIG. 30 are the consideration area. In this case, the consideration line is line L1. The line L1 is identical to a line dividing the area. In FIG. 30, it is assumed that the representative point T2 is more separated from the consideration line L1 than the representative point T1. Namely, with respect to the magnitudes of the components of the vectors that start from the division center point to the representative points T1 and T2, the components of the direction being parallel to the extending direction of the line that contacts the divided areas A1 and A2 of the consideration area and that starts from the division center point, the representative point T2 has greater magnitude that the representative point T1, so that the representative point T2 is the comparative representative point. The data point mores separated from the consideration line L1 than the comparative representative point T2 in the consideration area of the divided areas A1 and A2 (i.e., the data points having the component greater than that of the comparative representative point T2) are all of the data points excluding the two representative points T1 and T2. From among the data points, the data point having the greatest distance from the consideration line L1, namely data point T5 having the greatest magnitude of the component, is selected as the additional representative point.

Next, a case is described where it is assumed that the divided areas A2 and A3 constitute the consideration area and the same processes as described above are performed. In this case, the consideration line is line L2. The line L2 is identical to a line dividing the area. In the divided areas A2 and A3, the data point having the greatest distance from the consideration line L2 is the representative point T3. Therefore, there is no representative point to be added in this consideration area.

Next, a case is described where it is assumed that the divided areas A3 and A4 constitute the consideration area and the same processes as described above are performed. In this case, the consideration line is line L1. The representative point T4 is more separated from the consideration line L1 than the representative point T3. Therefore, the representative point T4 is a comparative representative point. From among the data points which are more separated from the consideration line L1 than the representative point T4, the data point having the greatest distance from the consideration line L1 is the data point T6. Therefore, the data point T6 is the additional representative point in this consideration area.

Next, a case is described where it is assumed that the divided areas A1 and A4 constitute the consideration area and the same processes as described above are performed. In this case, the consideration line is line L2. In the divided areas A1 and A4, the data point having the greatest distance from the consideration line L2 is the representative point T4. Therefore, there is no representative point to be added in this consideration area.

Figure 31:
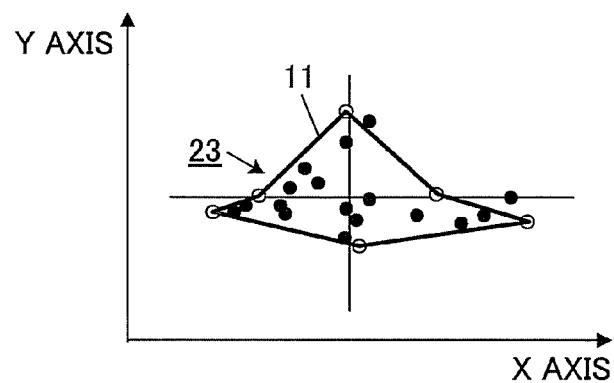
FIG. 31 is a drawing illustrating a result of the distribution representative point area defined by using the additional representative points illustrated in FIG. 30.

In this embodiment, finally, two (2) representative points T5 and T6 are determined to be added. FIG. 31 illustrates a result of the concentrated pattern defect distribution representative point area 11 defined by connecting the representative points T1 through T6, including the additional representative points T5 and T6, starting from any one of the representative points as the start point to the next representing point of the adjacent area with a line and further connecting in the same manner in clockwise or counterclockwise direction. As illustrated in FIG. 31, it may become possible to define the concentrated pattern defect distribution representative point area 11 including most of the data points of the data point distribution 23.

In the above embodiment, a case is described where from among the two representative points in the consideration area of two divided areas, one representative point more separated from the consideration line than the other representative point is used as the comparative representative point. However, in the distribution representative point selection step, it may not necessary to obtain the comparative representative point. When the comparative representative point is not obtained, by comparing the distances from the representative points in the consideration area to the consideration line, it may become possible to obtain the data point more separated from the consideration line than any other data point.

Further, in the above method according to an embodiment of the present invention, a case is described where the distribution area of the data points is divided into four (4) divided areas in a method in which a necessary representative point is added to define an appropriate distribution representative point area. However, the present invention is not limited to this configuration. Namely, the number of the divided areas is not limited to four (4). In the following, another exemplary case is described where the distribution area of the data points is divided into three (3) divided areas.

Figure 32:
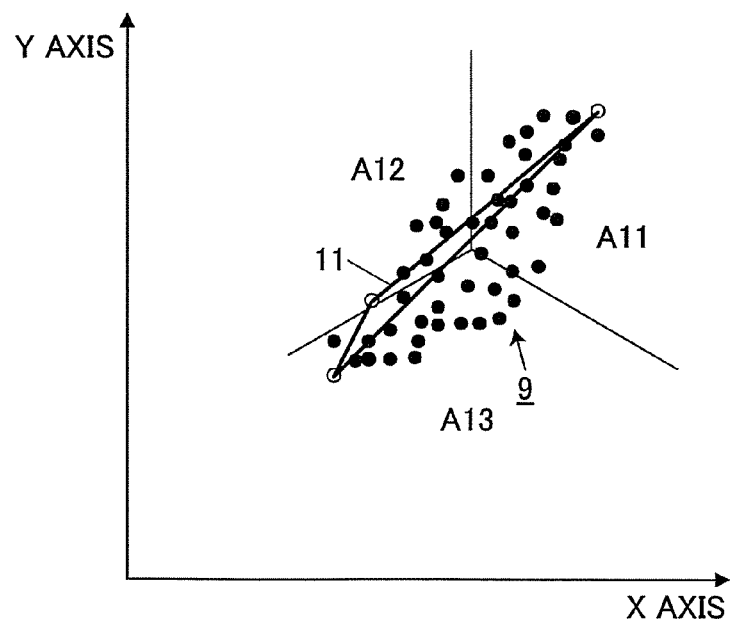
FIG. 32 is a drawing illustrating lines, the representative points, and the distribution representative point areas on the coordinate plane displaying the concentrated pattern defect distribution illustrated in FIG. 5.

FIG. 32 illustrates lines to divide the area into three (3) divided areas, the representative points of the divided areas, and the concentrated pattern defect distribution representative point area 11 on the coordinate plane expressing the concentrated pattern defect distribution 9 of FIG. 5. In FIG. 32, the gravity center of the data point distribution area is the division center point, the distribution area is divided into three (3) divided areas A11 through A13 in a manner such that the divided areas radiate from the division center point, and the representative point is obtained for each of the divided areas A11 through A13.

As illustrated in FIG. 32, the concentrated pattern defect distribution representative point area 11 defined by connecting the three (3) representative points of the respective divided areas A11 through A13 represents the data point distribution. However, to define more appropriate distribution representative area, it may be preferable to obtain additional representative point.

As a method of obtaining additional representative point, a method similar to the method described above may be used in which two (2) divided areas adjoining each other are defined as a consideration area, and vectors from the division center point to the positions of the data points are used. The magnitude (length) of the component of the vector in the direction parallel to the extending direction of the line that is between the two divided areas of the consideration area and that passes through the division center point is used (compared) as an index. In this case, in a method of obtaining the magnitude of the component, the consideration line as described above may be used.

However, the components of the data points in the direction parallel to the extending direction of the line contacting the divided areas A11 and A13 and starting the division center point may not be calculated by only addition and subtraction of the coordinate information of the data points and the coordinate information of the division center point.

Figure 33:
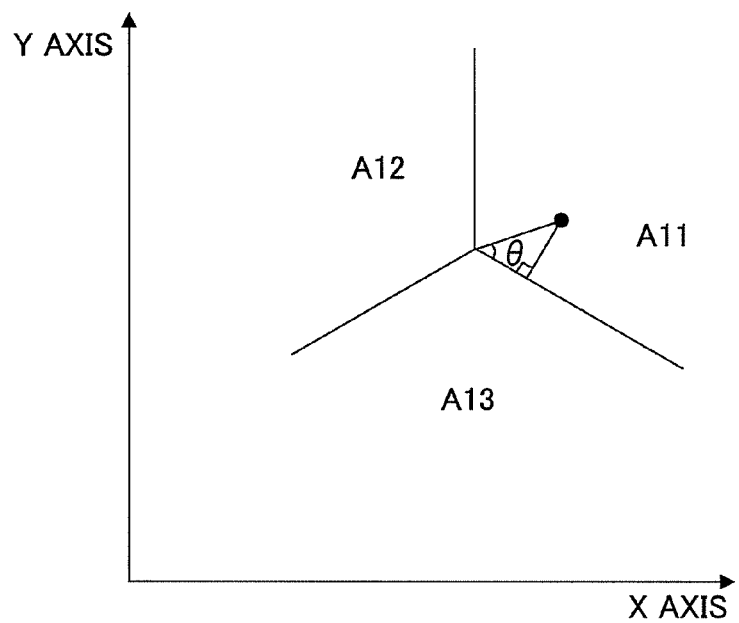
FIG. 33 is a drawing illustrating only one data point of the divided area A11 of FIG. 32.

In such a case, for example, a trigonometric function may be used to calculate the component. FIG. 33 illustrates one data of the data point in the divided area A11 from among the data points of FIG. 32.

In a vector starting from the division center point and terminating at the data point, the component of the vector in the direction parallel to the extending direction of the line (first line) that starts from the division center point and that contacts the divided areas A11 and A13 is equivalent to the vector starting from the division center point and terminating at a cross point between the first line and the perpendicular line from the data point to the first line. The divided areas A11 through A13 are given, the angle between the vector and the coordinate axis is obtained based on the coordinate information of the data point, the vector starting from the division center point and terminating at the data point. Therefore, the angle "θ" (see FIG. 33) between the line contacting the divided areas A11 and A13 and the vector starting from the division center point and terminating at the data point may be obtained. Therefore, the above component may also be obtained using a trigonometric function based on the distance between the division center point and the data point and the angle "θ".

Namely, (magnitude of the component)=(distance between the division center point and the data point)×cos θ

Based on the magnitude of the components of the data points in the consideration area obtained as described above, from among the data points having the magnitudes of the components greater than the magnitudes of the components of the representative points in the consideration area, the data point having a greatest magnitude of the component among all the data points is added as the (additional) representative point.

Figure 34:
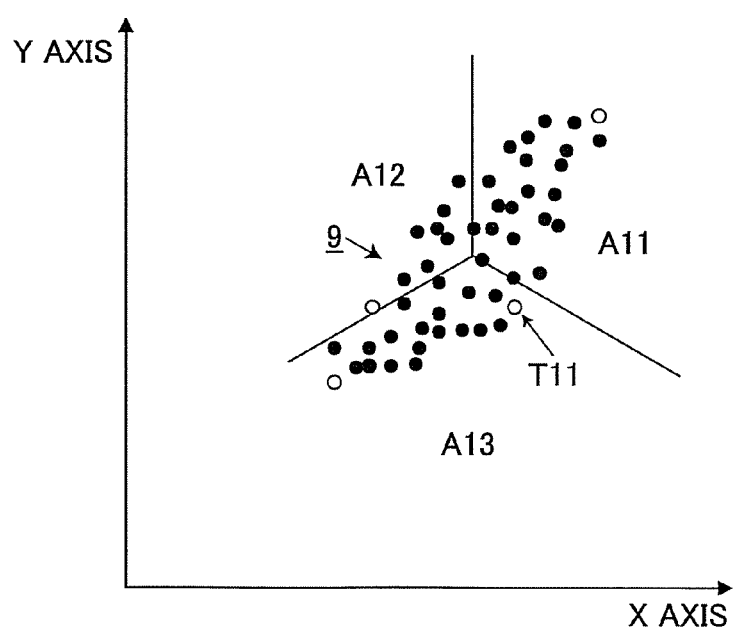
FIG. 34 is a drawing illustrating a result of obtaining an additional representative point to the data point distribution of FIG. 32.
Figure 35:
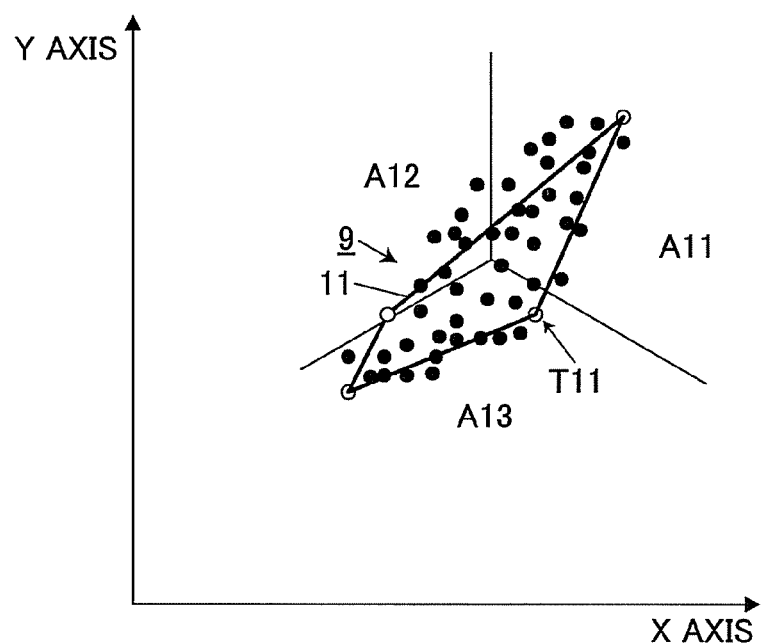
FIG. 35 is a drawing illustrating a result of the distribution representative point area defined by using the additional representative point of FIG. 34.

FIG. 34 illustrates a result of adding the additional representative point to the concentrated pattern defect distribution 9 of FIG. 32. FIG. 35 illustrates a result of the concentrated pattern defect distribution representative point area 11 defined by using the representative points in FIG. 34. As illustrated in FIG. 34, there is no representative point to be added in the consideration area of the divided areas A11 and A12. Similarly, there is no representative point to be added in the consideration area of the divided areas A12 and A13. On the other hand, in the consideration area of the divided areas A11 and A13, the data point T11 is the representative point to be added. When the four (4) representative points indicated in white circles in FIG. 34 are sequentially connected with lines from the representative point as the start point to the next and the following representative points, the concentrated pattern defect distribution representative point area 11 illustrated in FIG. 35 is defined. By doing in this way, more appropriate concentrated pattern defect distribution representative point area 11 may be defined.

Further, in the above embodiment, the consideration line is used when the magnitudes of the components of the vectors in the direction parallel to the extending direction of the line that contacts the divided two areas and that starts from the division center point, the vectors starting from the division center point and terminating at the respective data points. However, in an embodiment of the present invention, the consideration line may not be used. As the method of obtaining the magnitude of the component, any of various methods may be used. For example, as illustrated in FIG. 30, when there area two lines to divide the area into divided areas are parallel to the X axis and the Y axis, respectively, the magnitudes of the components may be obtained by using the coordinate components of the data points and the division center point in the direction parallel to the extending direction of the line contacting the two divided areas of the consideration area. However, the method of obtaining the magnitude of the component is not limited to the methods described above, and any other appropriate method may alternatively used.

Further, there is another method of obtaining the representative point to be added.

Another (a second) method of obtaining the representative point to be added is described.

When the representative point to be added is to be obtained, the magnitudes of the components of vectors in a direction are used as an index, the vectors starting from the division center point and terminating at the respective data points, the direction being parallel to the extending direction of a line starting from the division center point and contacting the divided areas. In this case, there is no concept of the consideration area. Further, from among the data points having greater magnitude of the component than any other representing points, the data point having the greatest magnitude of the component is added as the representative point. Further, there are plural directions of the lines each starting from the division center point and contacting the divided areas. Therefore, for each of the directions, the representative point may be added by using the magnitudes of the components of the data points as an index. When there are two or more data points that meets the above conditions in any of the directions, the data point closest to the division center point may be selected as the representative point.

Figure 36:
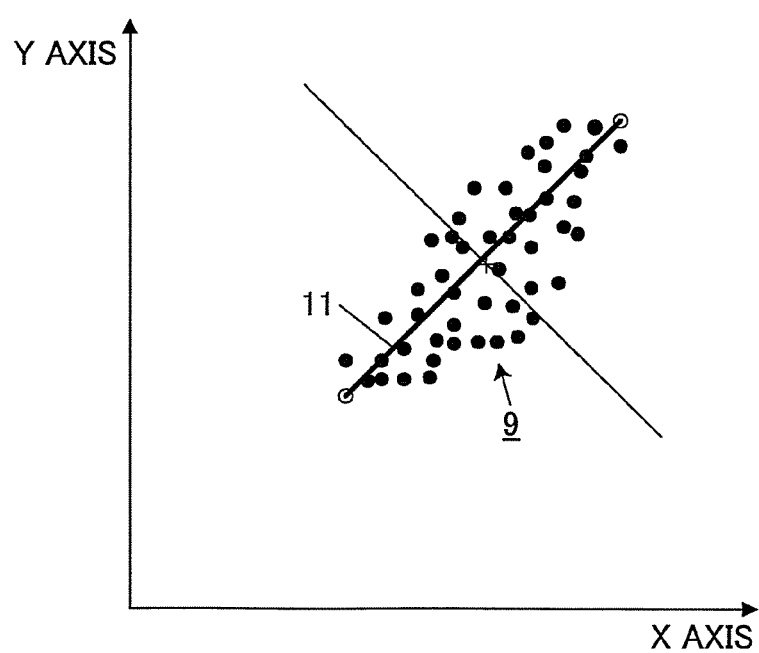
FIG. 36 is a drawing illustrating a line to divide the area into two (2) divided areas, the representative points, and the distribution representative point area on the coordinate plane displaying the concentrated pattern defect distribution illustrated in FIG. 5.

FIG. 36 illustrates a line to divide the area into two (2) divided areas, the representative points of the divided areas, and the concentrated pattern defect distribution representative point area 11 on the coordinate plane displaying the concentrated pattern defect distribution 9 of FIG. 5.

As illustrated in FIG. 36, the concentrated pattern defect distribution representative point area 11 defined by connecting the two (2) representative points of the respective two (2) divided areas indicates the data point distribution state of the concentrated pattern defect distribution 9. However, it may be preferable to obtain additional representative point to define more appropriate concentrated pattern defect distribution representative point area 11.

Figure 37:
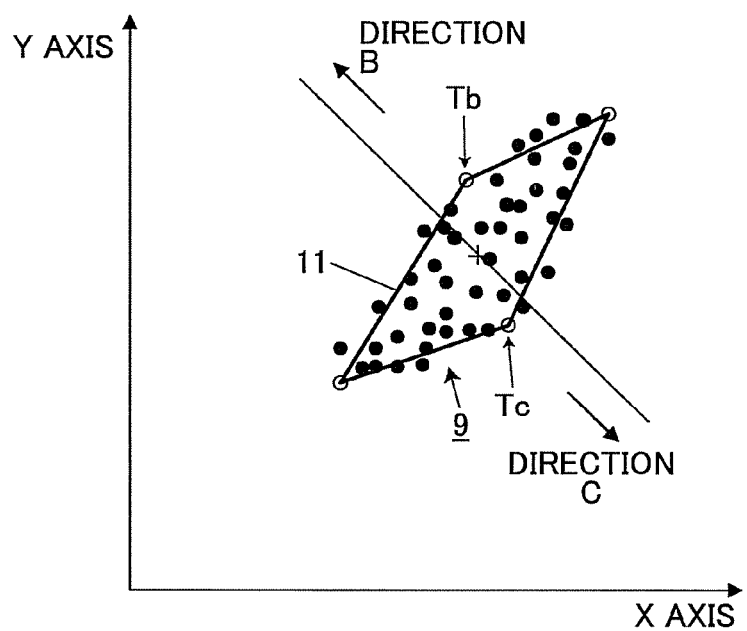
FIG. 37 is a drawing illustrating a result of distribution representative point area defined by using additional representative points added to the additional points of the concentrated pattern defect distribution of FIG. 36.

FIG. 37 illustrates a result of the concentrated pattern defect distribution representative point area 11 defined by using additional representative points added to the representative points of the concentrated pattern defect distribution 9 of FIG. 36.

In this embodiment, the second method of obtaining the representative point to be added is used. Specifically, additional representative points Tb and Tc are obtained for the directions B and C, respectively, in FIG. 37. The directions B and C corresponds the directions parallel to the extending directions of the line that starts from the division center point and that is used for the division of the area.

In this second method of obtaining the representative point to be added, similar to the method described above of obtaining the representative point to be added, the consideration line may be used.

However, as illustrated in FIGS. 36 and 37, namely when the line to divide the area is neither orthogonal nor parallel to the coordinate axes, the magnitudes of the components of the data points may not be calculated by only addition and subtraction of the coordinate information of the data points and the coordinate information of the division center point.

In such a case like this, it may be preferable to calculate the magnitudes of the components by using the trigonometric function as described in the case of the three (3) divided areas.

Based on the calculation of the magnitudes of the components using the trigonometric function, the data point Tb is determined (selected) as the representative point to be added in the B direction. Also, the data point Tc is determined (selected) as the representative point to be added in the C direction. FIG. 37 illustrates a result of the concentrated pattern defect distribution representative point area 11 defined by connecting four (4) representative points including two (2) representative points in FIG. 36 and two (2) representative points Tb and Tc in FIG. 37 starting from any one of the representative points as the start point to the next representing point of the adjacent area with a line and further connecting in the same manner in clockwise or counterclockwise direction. By doing in this way, more appropriate concentrated pattern defect distribution representative point area 11 may be defined.

Further, in this second method of obtaining the representative point to be added, the number of the divided areas divided from the data point distribution area is not limited to two (2). This second method may also be used when the number of the divided areas is three (3) or more.

Further, in the above description of step S5 with reference to FIGS. 1 and 4, cases are described where in the divided area including no data points, no representative data is determined or the coordinate of the division center point is the representative point of the divided area. The specific examples of the cases are described below with reference to FIGS. 38 through 40.

Figure 38:
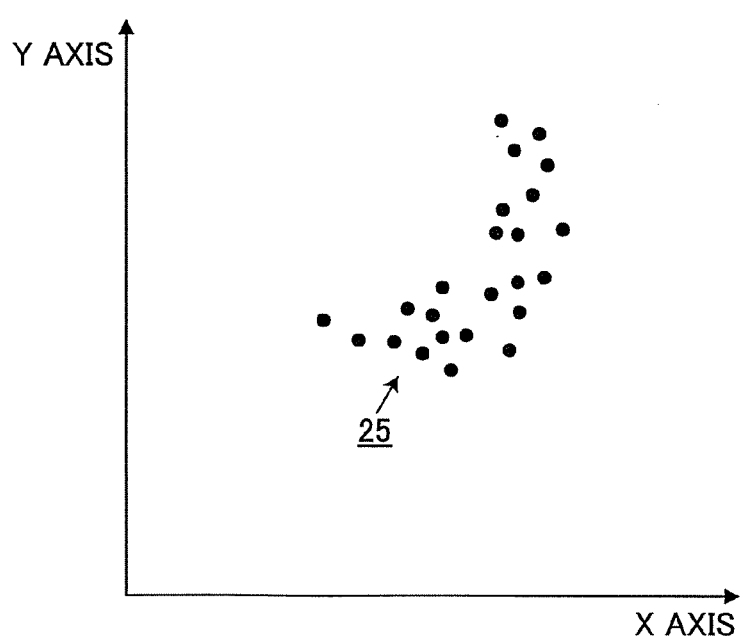
FIG. 38 is a drawing illustrating still another example of the data point distribution state on the coordinate plane.

FIG. 38 illustrates still another example of the data point distribution state on the coordinate plane.

Figure 39:
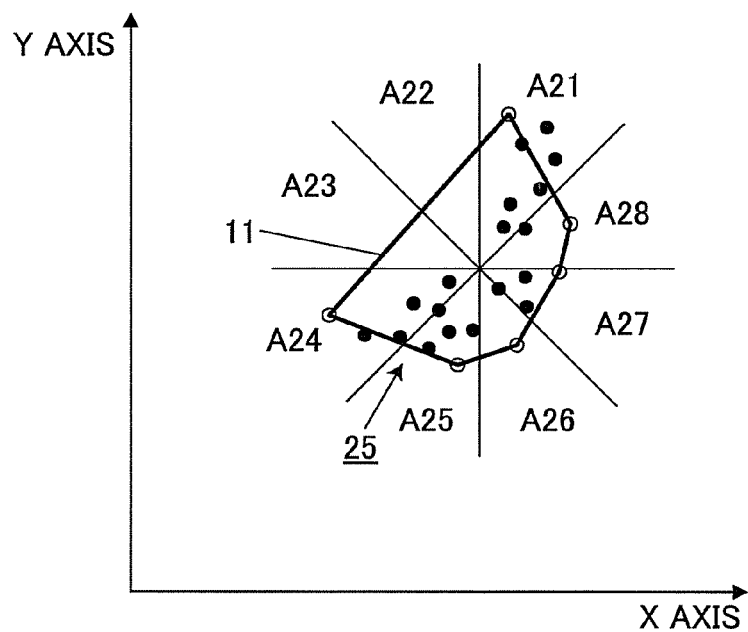
FIG. 39 is a drawing illustrating a result of the distribution representative point area by dividing the area of the data points of FIG. 38 into eight (8) divided areas.

FIG. 39 illustrates a result of the concentrated pattern defect distribution representative point area 11 defined by obtaining the representative points by performing the processes similar to the steps of steps S5-1, S5-2, and S5-3 of FIG. 4 on the data point distribution 25 of FIG. 38 and connecting the points with lines. In FIG. 39, the area is divided into eight (8) divided areas A21 through A28.

In FIG. 39, the divided areas A21 and A22 have no data points. Therefore, there is no representative point in the divided areas A21 and A22. In a case like this, when the divided area including no data point is generated (set), the size (area) of the defined concentrated pattern defect distribution representative point area 11 may be unnecessarily increased.

Figure 40:
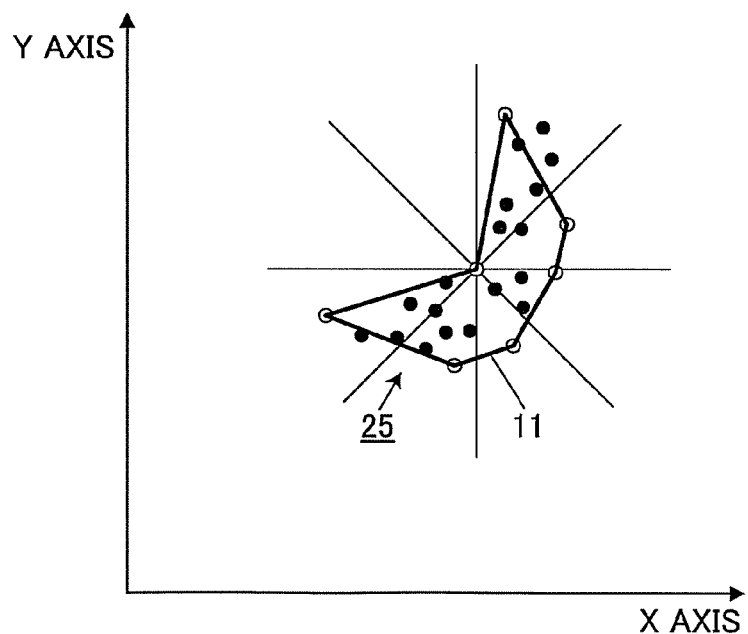
FIG. 40 is a drawing illustrating a result of the distribution representative point area by additionally using the division center point as an additional point added to the representative points of FIG. 39.

FIG. 40 illustrates the concentrated pattern defect distribution representative point area 11 defined by adding the representative point which is the division center point in addition to the representative points of FIG. 39. as illustrated in FIG. 40, by setting the division center point as the representative points of the divided areas A21 and A22 including no data points, it may become possible to define an appropriate concentrated pattern defect distribution representative point area 11 for the data point distribution 25.

Further, an embodiment of the present invention may also be applied to a process other than a process of information in semiconductor manufacturing. For example, an embodiment of the present invention may also be applied to a process of an image data. For example, there is a technique of recognizing various objects from an image data. As an example, there is a method of dividing a color image into the areas based on the color of the pixels (see, for example, Patent Documents 4 through 7).

Patent Document 4: Japanese Patent Application Publication No. 06-348991
Patent Document 5: Japanese Patent No. 3659914
Patent Document 6: Japanese Patent Application Publication No. 2007-072987
Patent Document 7: Japanese Patent No. 3709879

Figure 41:
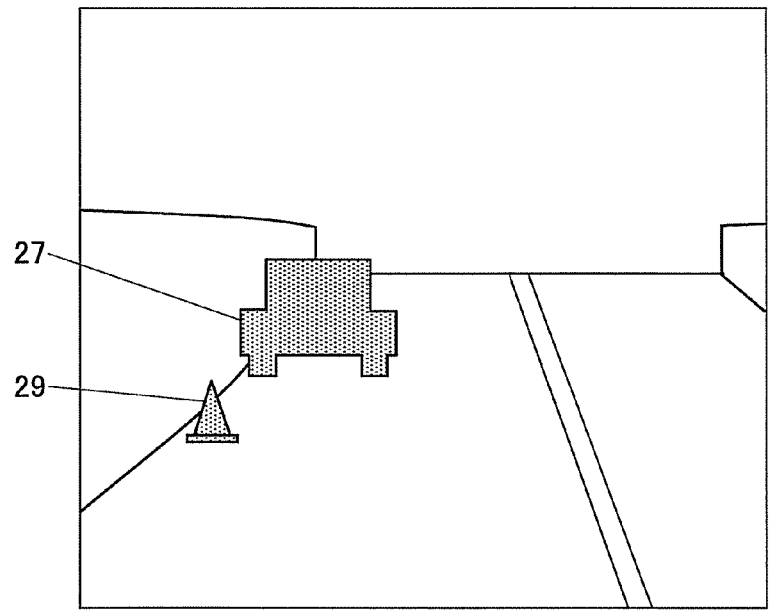
FIG. 41 is an image acquired (captured) by a moving vehicle.

FIG. 41 illustrates an image of a parked vehicle and a road cone on a road acquired by a moving vehicle.

When a known technique of acknowledging various objects from image data is used, it is possible to acknowledge (detect) a parked vehicle area 27 and a road cone area 29 (see FIG. 41). The pixels depicting the parked vehicle area 27 and the road cone area 29 are group XY coordinate data and can be the data group to be determined. Therefore, the above-described steps of the method according to an embodiment of the present invention may also be applied to such group XY coordinate data.

Further, when the area of an image data is divided only based on the colors or the gray values, it may not be possible to acknowledge what is the actual object corresponding to the image data. However, it may not be always necessary to acknowledge what is the actual object corresponding to the image data when the purpose is, for example, to ensure (determine) the possibility of contact between the detected object and the moving vehicle.

Herein, for example, it is assumed that the occupied area of the moving vehicle is the determination area, and that the unknown detected object is an obstacle. First, the representative points expressing the occupied area of the obstacle (corresponding to the data point distribution area of the data group to be determined) are obtained. Then, by connecting the obtained representative points with lines, the distribution representative point area is obtained. Next, it is determined whether there is the overlapping area where the determination area overlaps the distribution representative point area.

For example, in the case of the image of FIG. 41, in order to ensure the possibility of the contact between the parked vehicle or the road cone (i.e., the detected object) and the moving vehicle when the vehicle passes beside the parked vehicle or the road cone, it is assumed that the area occupied by the moving vehicle in the image is the determination area. First, the representative points of the parked vehicle area 27 and the road cone area 29 are obtained. Then, the distribution representative point area is defined by connecting the obtained representative points with lines. Next, it is determined whether there is the overlapping area where the determination area overlaps the distribution representative point area.

Figure 42:
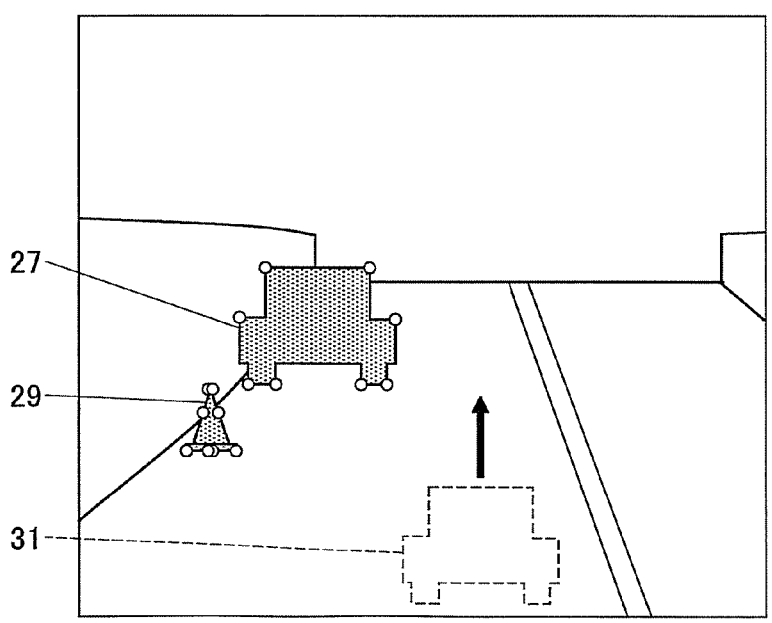
FIG. 42 is a drawing illustrating the representative points of the data point distribution area of the parked vehicle area and road cone area of FIG. 41.

FIG. 42 illustrates the representative points of the data point distribution area of the parked vehicle area 27 and the road cone area 29. Herein, the area is divided into eight (8) divided areas, and then, the representative points (displayed in white circles) are obtained. Further, it is assumed that the moving vehicle moves in the arrow direction.

Figure 43:
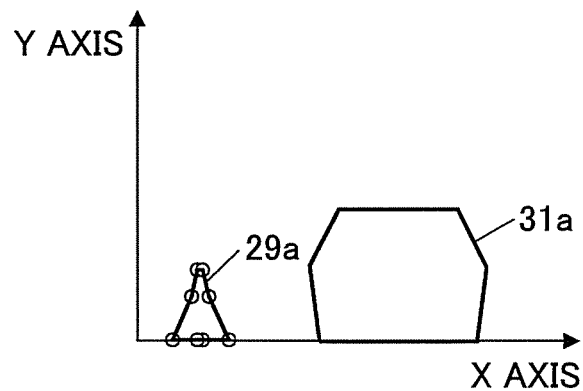
FIG. 43 is a drawing illustrating a determination area and distribution representative point area of the road cone area on the coordinate when the moving vehicle passes near the road cone.

FIG. 43 illustrates the determination area and the distribution representative area of the road cone area on the coordinate plane when the moving vehicle passes beside the road cone. In this case, there is no overlapping area where the determination area 31a corresponding to the moving vehicle overlaps the distribution representative point area 29a corresponding to the road cone area 29. Therefore, it is determined that the moving vehicle does not contact the road cone.

Figure 44:
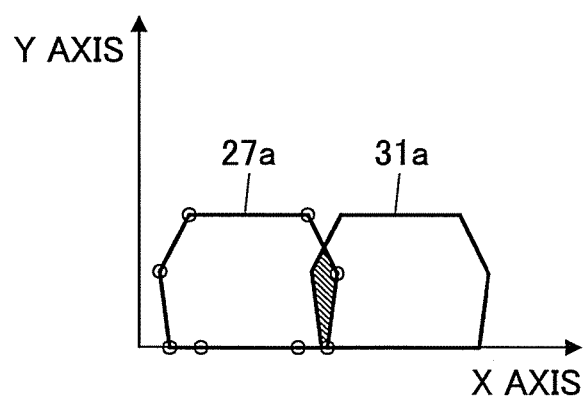
FIG. 44 is a drawing illustrating a determination area and distribution representative point area of the parked vehicle area on the coordinate plane when the moving vehicle passes near the parked vehicle area.

FIG. 44 illustrates the determination area and the distribution representative area of the parked vehicle area 27 on the coordinate plane when the moving vehicle passes beside the parked vehicle. In this case, there is the overlapping area where the determination area 31a corresponding to the moving vehicle overlaps the distribution representative point area 27a corresponding to the parked vehicle area 27. Therefore, it is determined that the moving vehicle contacts the road cone.

On the other hand, as a recognition method of an image, there is a known method such as pattern matching. However, in an method according to an embodiment of the present invention, it may also be possible to recognize an object of an image.

One example is described. The information of the representative points corresponding to the shapes of the various objects on a road displayed on a screen is registered in a database. For example, the image acquired from the moving vehicle includes, but not limited to, the parked vehicle area 27, the road cone area 29, and road sign areas 33 and 35.

Figure 46:
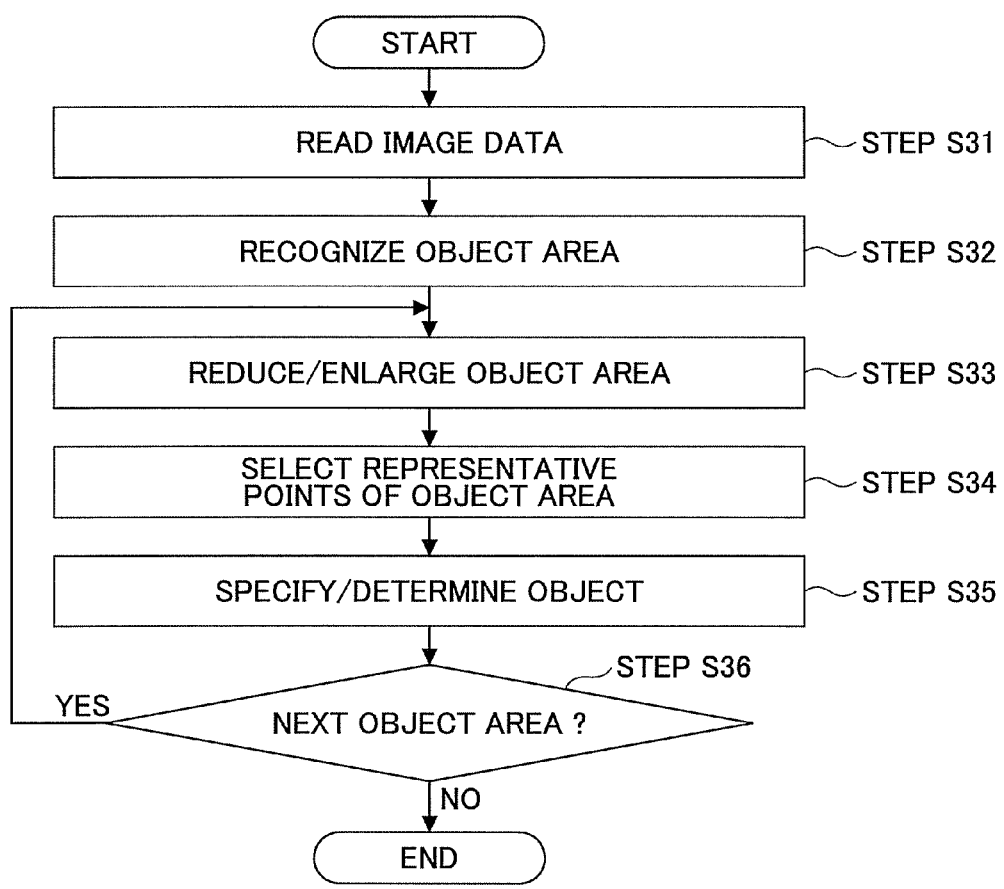
FIG. 46 is a flowchart illustrating a process of specifying an object area displayed in the image.

FIG. 46 is a flowchart illustrating a process of specifying an object area displayed on an image.

Figure 45:
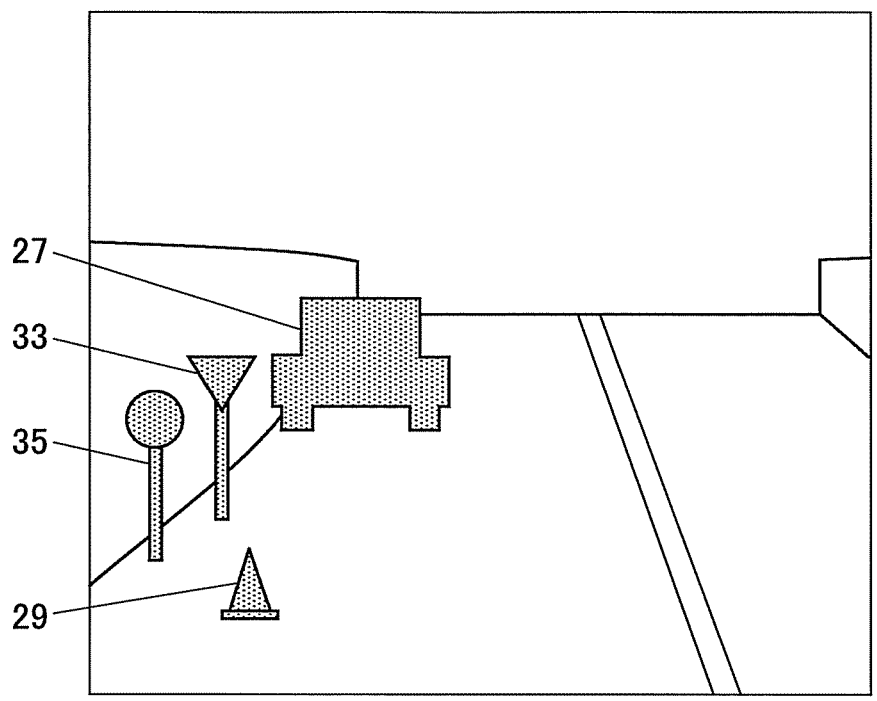
FIG. 45 is another example of the image acquired by the moving vehicle.
Figure 47:
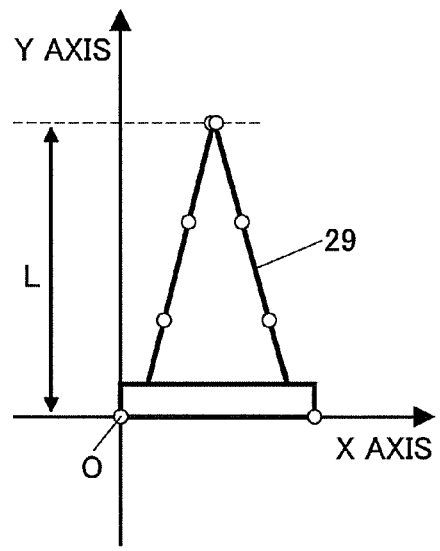
FIG. 47 is a drawing illustrating the road cone area of FIG. 45, and a reference point and the representative points of the road cone area.

Step S31: Image data are read.
Step S32: The object area in the image data (i.e., the data point distribution area of the data group to be determined) is recognized. For example, in the image of FIG. 45, the parked vehicle area 27, the road cone area 29, and the road sign areas 33 and 35 are recognized.
Step S33: The first object area is reduced or enlarged so that the height or the width of the first object area is equal to a predetermined length. For example, as illustrated in FIG. 47, the road cone area 29 is reduced or enlarged in a manner such that when a reference point "O" has X coordinate value and Y coordinate value equal to the minimum X coordinate value and the minimum Y coordinate value, respectively, of the data points in the road cone area 29, the length in the height direction of the road cone area 29 is equal to the length L.
Step S34: In the coordinate plane where the reference point "O" determined in step S33 is set to the original point of the coordinate plane, the representative points of the object area are obtained. The method of obtaining the representative points is described above. For example, the gravity center of the object area is the division center point, and the area of the coordinate plane is divided into eight (8) divided areas to determine the representative points. In FIG. 47, the representative points of the road cone area 29 are displayed in white circles.
Step S35: For each of the plural determination areas that have been registered in advance, the area of the overlapping area where the distribution representative point area overlaps the determination area is obtained, the distribution representative point area being obtained by connecting the representative points with lines. For example, if there is an object that corresponds to a case where the ratio of the area of the overlapping area to the area of the determination area is equal to or greater than a first ratio threshold value, herein 80%, and the ratio of the area of the overlapping area to the area of the distribution representative point are is equal to or greater than a second ratio threshold value, herein 80%, the name of the object is determined as the name of the object corresponding to the distribution representative point area. In this case, for example, the determination areas including, but not limited to, a vehicle determination area, a road cone determination area, a first road sign determination area, a second road sign determination area and the like are registered.

Figure 48:
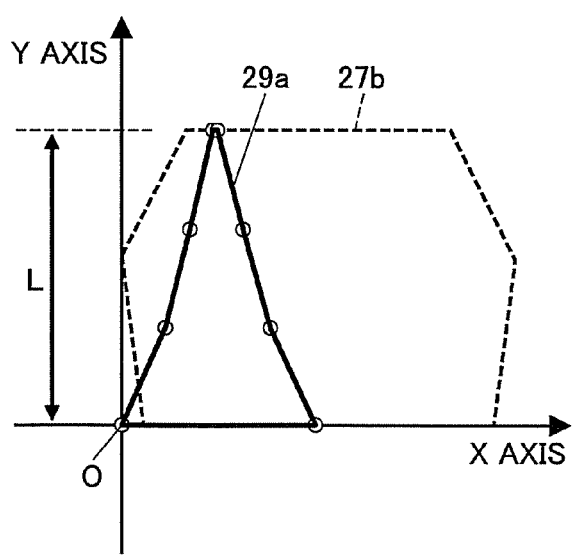
FIG. 48 is a drawing illustrating a road cone distribution representative point area and a vehicle determination area.
Figure 49:
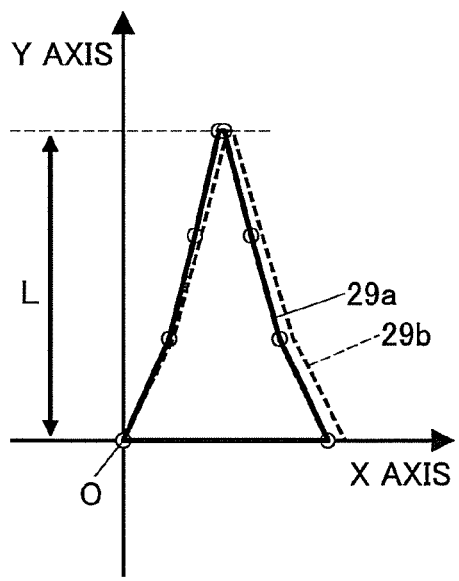
FIG. 49 is a drawing illustrating the road cone distribution representative point area and a road cone determination area.
Figure 50:
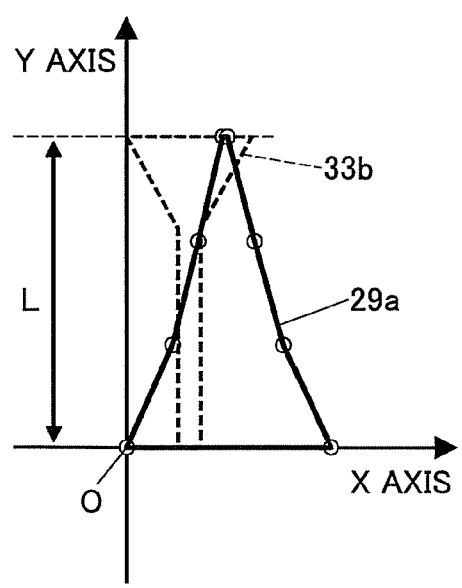
FIG. 50 is a drawing illustrating the road cone distribution representative point area and a first road sign determination area.

FIG. 48 illustrates the road cone distribution representative point area and the vehicle determination area. FIG. 49 illustrates the road cone distribution representative point area and the road cone determination area. FIG. 50 illustrates the road cone distribution representative point area and the first road sign determination area. The heights of the vehicle determination area 27b in FIG. 48, the road cone determination area 29b in FIG. 49, and the first road sign determination area 33b in FIG. 50 are set to be equal to the length L.

As illustrated in FIG. 48, most of the road cone determination area 29b obtained by connecting the representative points of the road cone area 29 overlaps the vehicle determination area 27b.

Further, in this case, the ratio of the area of the overlapping area between the areas 27b and 29a to the area of the road cone distribution representative point area 29a is, for example, approximately 95%, which is greater than the predetermined second ratio threshold value (80%).

However, the ratio of the area of the overlapping area between the areas 27b and 29a to the area of the vehicle determination area 27b is, for example, approximately 25%, which is less than the predetermined first ratio threshold value (80%).

Therefore, the data group of the road cone area 29 (data group to be determined) is not the relevant data corresponding to the vehicle determination area 27b (determination area).

As illustrated in FIG. 49, most of the road cone determination area 29a overlaps the road cone determination area 29b.

Further, in this case, the ratio of the area of the overlapping area between the areas 29a and 29b to the area of the road cone distribution representative point area 29a is, for example, approximately 95%, which is greater than the predetermined second ratio threshold value (80%).

Further, the ratio of the area of the overlapping area between the areas 29a and 29b to the area of the road cone determination area 29b is, for example, approximately 90%, which is greater than the predetermined first ratio threshold value (80%).

Therefore, the data group of the road cone area 29 (data group to be determined) is the relevant data corresponding to the road cone determination area 29b (determination area).

As illustrated in FIG. 50, the overlapping area between the road cone distribution representative point area 29a and the first road sign determination area 33b is smaller when compared with the case of FIG. 49.

Further, in this case, the ratio of the area of the overlapping area between the areas 29a and 33b to the area of the road cone distribution representative point area 29a is, for example, approximately 15%, which is less than the predetermined second ratio threshold value (80%).

Further, the ratio of the area of the overlapping area between the areas 29a and 33b to the area of the first road sign determination area 33b is, for example, approximately 40%, which is less than the predetermined first ratio threshold value (80%).

Therefore, the data group of the road cone area 29 (data group to be determined) is not the relevant data corresponding to the first road sign determination area 33b (determination area).

Similarly, the area of the overlapping area between the road cone distribution representative point area 29a and the second road sign determination area has a similar value in the case of FIG. 50. Therefore, the data group of the road cone area 29 (data group to be determined) is not the relevant data corresponding to the second road sign determination area (determination area).

Figure 51:
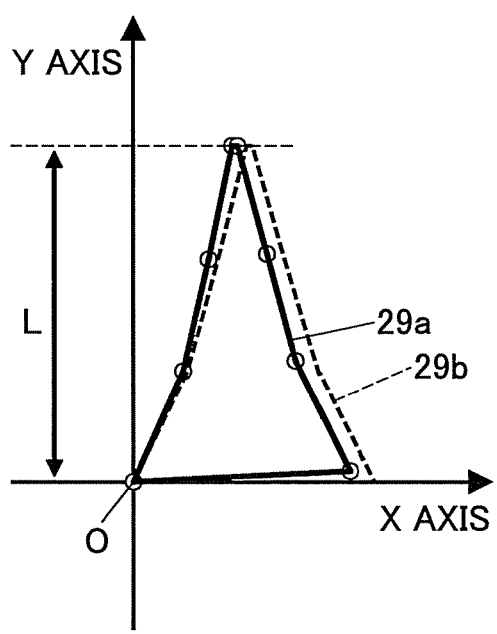
FIG. 51 is a drawing illustrating another example of the road cone distribution representative point area and the road cone determination area.

Further, for example, depending on the angle of image acquisition, even when the shape of the road cone area 29, particularly, the shape of the road cone distribution representative point area 29*a* slightly differs from the shape of the road cone determination area 29*b*, as illustrated in FIG. 51, most of the road cone distribution area 29*b* overlaps the road cone determination area 29*b*. For example, in FIG. 51, the ratio of the area of the overlapping area between the areas 29*a* and 29*b* to the road cone distribution representative point area 29*a* is approximately 90%, which is greater than the predetermined first ratio threshold value (80%).

As described above, even in a case of FIG. 51, the data group of the road cone area 29 (data group to be determined) is the relevant data corresponding to the road cone determination area (determination area). As a result, it is specified that the road cone area 29 represents the road cone.

Step S36: It is determined whether there is any object area that is recognized in step S32 and that is not yet processed. For example, when there is an object area that is not yet processed, the object area including the parked vehicle area 27, the road sign areas 33 and 35, or the like (YES in step S36), the process goes back to step S33 to perform the processes in steps S33 and S34 to specify the name of the object in the object area. On the other hand, when there is no object area to be processed (NO in step S36), the process ends.

As described above, an embodiment of the present invention may also be applied to the recognition of an image.

Further, when the representative information of the object area is associated with the object name information and recorded in a database first, the representative point information may be used to specify the object name.

Figure 52:
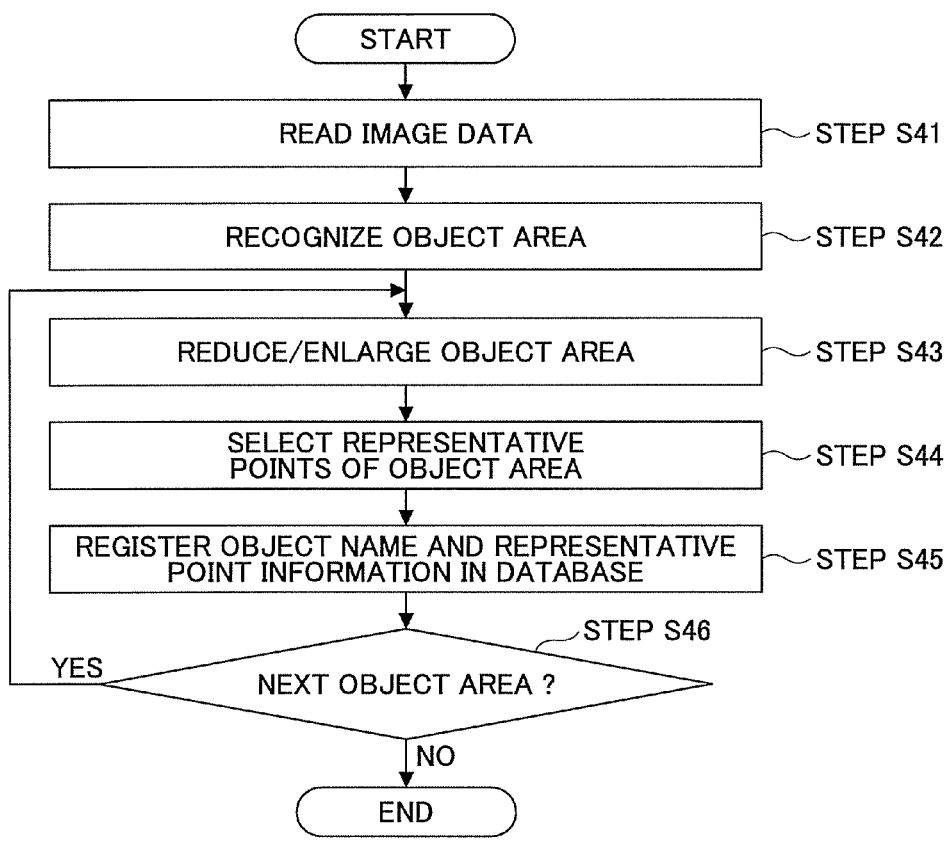
FIG. 52 is a flowchart illustrating a process of making a database of representation point information of the object area displayed in the image.

FIG. 52 is a flowchart illustrating a process of making a database of the representative point information of the object information displayed on an image.

Steps S41 through S44: Similar to steps S31 through S34 described with reference to FIG. 46, an image data are read, an object area (data point distribution area of the data group to be determined) in the image data is recognized, the object area is reduced or enlarged, and the representative points of the object area are selected.

Step S 45: The representative point information acquired in step S44 is associated with the object name information (identification information of the data group to be determined) and registered in a database.

Step S46: It is determined whether there is an object area that is not yet registered. When determining that there is an object area (next area) that is not yet registered (YES in step S46), the process goes back to step S43 to perform the processes in steps S43 through S45 for the next area. On the other hand, when determining that there is no object area (next area) that is not yet registered (NO in step S46), the process ends.

Figure 53:
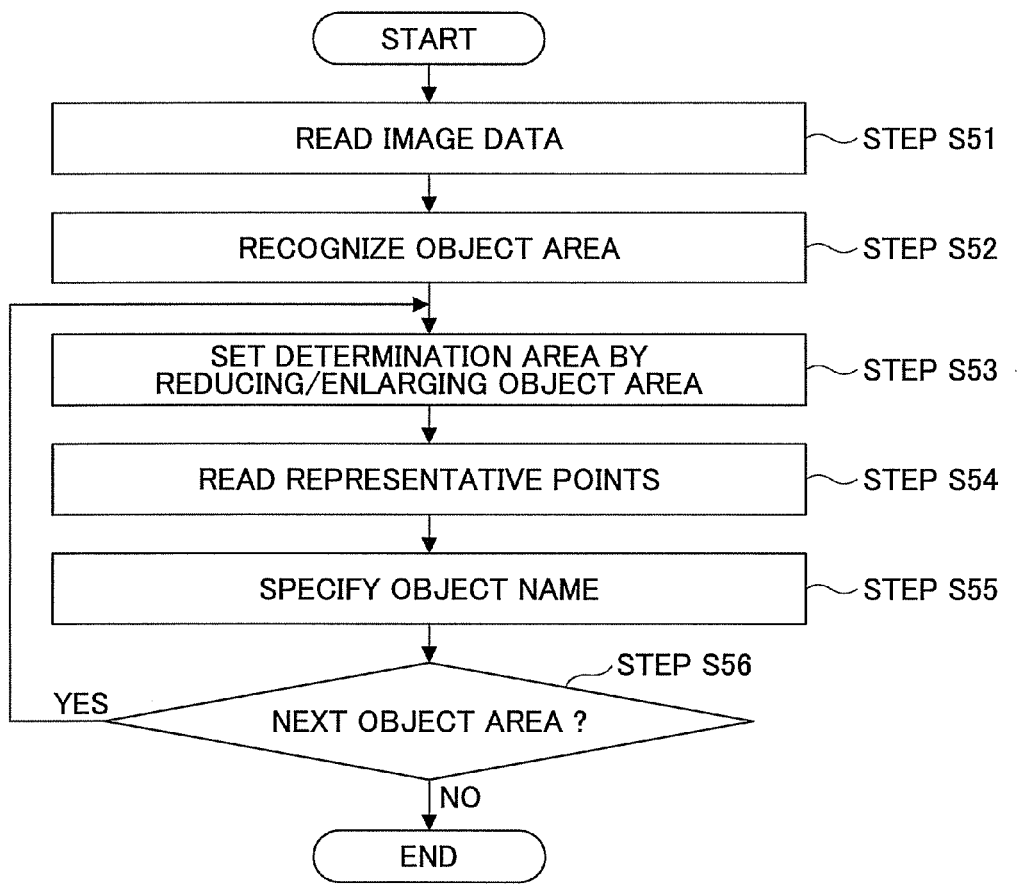
FIG. 53 is a flowchart illustrating a process of specifying an object in the image based on the representative point information in database.

FIG. 53 is a flowchart illustrating a process of specifying an object in an image based on the representative point information in a database.

Step S51: Image data are read.

Step S52: An object area in the image data is recognized.

Step S53: The object area is reduced or enlarged in a manner such that the height or the width of a first object area is equal to a predetermined length. For example, the object area is reduced or enlarged in a manner such that the length in the height direction of the object area is equal to a predetermined length by setting a reference point having the x and y coordinate values equal to the minimum X and Y coordinate values of the data points in the object area. The reduced or enlarged object area is set as the determination area.

Step S54: The representative points for each of the object name information registered in the database are read.

Step S55: For each of the object name information, the distribution representative point area is defined by connecting the read representative points of the object name information. For each of the object name information, the area of the overlapping area between the determination area obtained in step S53 and the distribution representative point area is obtained. The object name of the object name information having the greatest area of the overlapping area is specified as the object name of the object area corresponding to the determination area.

Step S56: It is determined whether there is an object area that is not yet determined. When determining that there is an object area (next object area) that is not yet determined (YES in step S56), the process goes back to step S53 and performs the processes of steps S53 through S55 on the next object area. On the other hand, when determining that there is no object area (next object area) that is not yet determined (NO (NO in step S56), the process ends.

As described above, the representative point information registered in the database may also be used for specifying the object name.

In the above description, when the points representing the shape of the object area are to be obtained, the XY coordinate values of the reference point are the minimum X value and the minimum Y value of the data points of the object area. However, the reference value is not limited to this configuration.

For example, the reference value may have the X and Y coordinate values equal to the median values between the minimum X and Y and the maximum X and Y values, respectively of the object area. The reference point is determined based on the same definition when database is made and when the determination area is obtained.

In the above description, the representative point is expressed using the XY coordinate system. However, the representative point may be expressed using the polar coordinate system.

Further, when the database of the representative points of the object area is made, it may be preferable to register the information expressing the feature of the distribution representative point area in addition to the representative points information. For example, the information expressing the feature of the distribution representative point area includes an index indicating whether the shape of the distribution representative points area is vertically long or laterally long, the roundness rate described above and the like, so as to be associated and registered in the database. Further, color information of the object area may also be registered in the database as the information indicating the feature of the object area.

As described above, when the information indicating the feature of the object area is registered, it may become possible to limit the recognition target by using the information in specifying the object area.

Further, in the above embodiment, an object in the acquired image data may be specified. In addition, an embodiment of the present invention may also be applied to detect an area having a specific shape in the acquired image data.

A specific technical field where an embodiment of the present invention may be used is to detect an alignment mark of two-dimensional bar code and detect an alignment mark when sizes are measured in a semiconductor manufacturing process.

As described above, an embodiment of the present invention may also be applied to processes other than the processes performed on the information in a semiconductor manufacturing.

Each of the steps in the embodiments described above may be realized by creating a program for executing the steps and causing the computer to execute the created program.

According to an embodiment of the present invention, there is provided an identification method of identifying a data point distribution area on a coordinate plane. The identification method includes a distribution representative point selection step of dividing an area on the coordinate plane into two or more divided areas in a manner such that the divided areas radiate from a division center point, the division center point being an arbitrary point and a center point of the divisions, plural data being expressed as data points on the coordinate plane, the plural data constituting a data group to be determined, each of the plural data including two variables as a pair, the data point distribution area being a distribution area of the data points, and selecting, in each of the divided areas, from among the data points in the divided area, a data point having the greatest distance from the division center point as a representative point of the data point distribution area; and a determination step of determining whether there is an overlapping area where a distribution representative point area overlaps a determination area, the distribution representative point area being defined by connecting the representative points with lines, the determination area being a specific area set on the coordinate plane, and determining, when determining that there is the overlapping area, that the data group to be determined is a relevant data group.

Herein, as the coordinate plane, any appropriate coordinate plane such as the orthogonal coordinate plane, the oblique coordinate plane, the polar coordinate plane or the like may be used Further, the number of divided areas on the coordinate plane is two or more.

Further, the data point on the border line between two adjoining divided areas may be treated as the data point of each of the two divided areas or the data point of either one of the two divided areas. In the latter case, it may be defined in advance whether the data point on the border line is to be treated as the data point of which of the adjoining divided areas. For example, when the area of the coordinate plane is divided into three (3) or more divided areas, it may be determined in advance that the data point on the border line is to be treated as the data point on the divided area which is on the proceeding direction side in the clockwise or counterclockwise direction.

Further, the data group to be determined may be any one of pattern defect inspection result data, particle inspection result data, and wafer test result data in a semiconductor device manufacturing process. However, the data group to be determined is not limited to those data.

Further, the identification method of identifying a data point distribution area on a coordinate plane may further include a representative point information registration step of associating and registering information of the representative points acquired in the distribution representative point selection step with information to be used to identifying the data group to be determined into a database, in which the representative point information registration step is performed before the determination step is performed, and in the determination step, it is determined whether there is the overlapping area by reading the information of the representative points associated with the information to be used to identifying the data group to be determined from the database.

Further, in the representative point information registration step, characteristic information may be associated with the information to be used to identifying the data group to be determined and stored in the database, the characteristic information including a distribution range of the data point distribution area, a distribution range of the distribution representative point area, and at least one of an area, a roundness rate, and a data point distribution density of the distribution representative point area; and in the determination step, after making a short list of the data group to be determined based on the characteristic information, it may be determined whether there is the overlapping area.

Herein, the information indicating the distribution range of the data point distribution area is expressed by the maximum value and the minimum value in the X axis and the maximum value and the minimum value in the Y axis from among the XY coordinate values of the data points included in the data point distribution area or by the maximum r value, the minimum r value, the maximum θ value, and the minimum θ value of the data point distribution area of the polar coordinate values.

Further, the information indicating the distribution range of the distribution representative point area is expressed by the maximum value and the minimum value in the X axis and the maximum value and the minimum value in the Y axis from among the XY coordinate values of the data points included in the distribution representative point area or by the maximum r value, the minimum r value, the maximum θ value, and the minimum θ value of the distribution representative point area of the polar coordinate values.

Further, in the determination step, it may be determined whether an area of the distribution representative point area is equal to or greater than a predetermined distribution representative point area threshold value, and when determining that the area of the distribution representative point area is less than the distribution representative point area threshold value, it may be determined that the data group to be determined is not the relevant data group.

Further, in the determination step, it may be further determined whether an area of the overlapping area is equal to or greater than a predetermined overlapping area point area threshold value, and when determining that the area of the overlapping area is equal to or greater than the overlapping area threshold value, it may be determined that the data group to be determined is the relevant data group.

Further, in the determination step, it may be further determined whether a ratio of an area of the overlapping area to an area of the determination area is equal to or greater than a predetermined first ratio threshold value, and when determining that the ratio of the area of the overlapping area to the area of the determination area is equal to or greater than the predetermined first ratio threshold value, it may be determined that the data group to be determined is the relevant data group.

Further, in the determination step, it may be further determined whether a ratio of an area of the overlapping area to an area of the distribution representative point area is equal to or greater than a predetermined second ratio threshold value, and when determining that the ratio of the area of the overlapping area to the area of the distribution representative point area is equal to or greater than the predetermined second ratio threshold value, it may be determined that the data group to be determined is the relevant data group.

Further, any combination of the process using the predetermined distribution representative point area threshold value, the process using the predetermined overlapping area point area threshold value, the process using the predetermined first ratio threshold value, and the process using the predetermined second ratio threshold value may be performed. Namely, for example, some of the processes may be performed, or all of the processes may be performed.

Further, in the determination step, the distribution representative point area may be defined by sequentially connecting the representative points with lines in a manner such that the lines are not crossed over each other.

Further, in the representative point information registration step, a center or a gravity center of the data point distribution area of the data group to be determined may be selected as the division center point.

Herein, the center of the data point distribution area of the data group to be determined refers to a point having values for respective variables of the data points included in the data point to be determined, each of the values being obtained by obtaining a sum of the maximum value and the minimum value and then dividing the sum by 2. Further, the gravity center of the data point distribution area of the data group to be determined refers to a point having values for respective variables of the data points included in the data point to be determined, each of the values being an averaged value of the variable.

Further, in the distribution representative point selection step, when there is a divided area including no data point, the division center point may be selected as the representative point.

However, even when there is a divided area including no data point, it is not always necessary to select the division center point as the representative point.

Further, in the distribution representative point selection step, after the representative points are selected, two divided areas adjoining each other may be set as a consideration area, in the consideration area, vectors starting from the division center point and terminating at the data points may be provided, from among the data points having magnitudes of a component of the vectors, the magnitudes being greater than magnitudes of the component of the representative points, the component referring a direction parallel to an extending direction of a line that starts from the division center point and that contacts the two divided areas of the consideration area, a data point having the greatest magnitude may be added as the representative point.

Further, when there are two or more data points having the greatest magnitude of the component in the consideration area, the data point closest to the division center point may be added as the representative point.

Further, in the distribution representative point selection step, after the representative points are selected, vectors starting from the division center point and terminating at the data points may be provided, in each of the directions parallel to extending directions of the lines that start from the division center point and that are used to divide the area on the coordinate plane into the divided areas, from among the data points having magnitudes of the component of the vectors, the magnitudes being greater than magnitudes of the component of the representative points, a data point having the greatest magnitude may be added as the representative point.

Further, when there are two or more data points having the greatest magnitude in the direction parallel to extending direction of the line that starts from the division center point and that is used to divide the area on the coordinate plane into the divided areas, the data point closest to the division center point may be added as the representative point.

According an embodiment of the present invention, there is provided a non-transitory computer-readable recording medium including a program encoded and stored in a computer readable format to cause a computer to execute the steps described above.

In an identification method according to an embodiment of the present invention, an area on the coordinate plane is divided into two or more divided areas in a manner such that the divided areas radiate from a division center point, the division center point being an arbitrary point and a center point of the divisions, plural data being expressed as data points on the coordinate plane, the plural data constituting a data group to be determined, each of the plural data including two variables as a pair, the data point distribution area being a distribution area of the data points, and in each of the divided areas, from among the data points in the divided area, a data point having the greatest distance from the division center point is selected as a representative point of the data point distribution area (distribution representative point selection step). Further, it is determined whether there is an overlapping area where a distribution representative point area overlaps a determination area, the distribution representative point area being defined by connecting the representative points with lines, the determination area being a specific area set on the coordinate plane, and when determining that there is the overlapping area, it is determined that the data group to be determined is a relevant data group (determination step).

By doing in this way, it may become possible to determine whether the data point distribution area of the data group to be determined is distributed in a specific determination area while the data point distribution area has been replaced by the distribution representative point area, in other words while the information amount expressing the data point distribution area has been decreased.

Further, in an identification method according an embodiment of the present invention, the data group to be determined may be any one of pattern defect inspection result data, particle inspection result data, and wafer test result data in a semiconductor device manufacturing process.

By doing this, it may become possible to extract a lot having wafers having similar pattern defect distribution status, particle (contamination, foreign matter) defect distribution status, or defect chip distribution status, so as to estimate the cause of defect caused by the manufacturing apparatuses and manufacturing processes.

Further, in the identification method according an embodiment of the present invention, the information of the acquired representative points may be associated with information to be used to identifying the data group to be determined and registered into a database (representative point information registration step). In this case, the representative point information registration step is performed before the determination step is performed, and in the determination step, it is determined whether there is the overlapping area by reading the information of the representative points associated with the information to be used to identifying the data group to be determined from the database.

By doing in this way, it may not be necessary to perform the process of the distribution representative point selection step every time to perform the process of the determination step for the data group to be determined such as the pattern defect inspection result data, the particle inspection result data, and the wafer test result data, thereby enabling reducing the processing time.

Further, in the representative point information registration step, characteristic information may be associated with the information to be used to identifying the data group to be determined and stored in the database, the characteristic information including a distribution range of the data point distribution area, a distribution range of the distribution representative point area, and at least one of an area, a roundness rate, and a data point distribution density of the distribution representative point area; and in the determination step, after making a short list of the data group to be determined based on the characteristic information, it may be determined whether there is the overlapping area.

By doing in this way, it may become possible to reduce the number of the data groups to be determined, thereby enabling reducing the processing time.

Further, in an identifying method according to an embodiment of the present invention, in the determination step, it may be determined whether an area of the distribution representative point area is equal to or greater than a predetermined distribution representative point area threshold value, and when determining that the area of the distribution representative point area is less than the distribution representative point area threshold value, it may be determined that the data group to be determined is not the relevant data group.

By doing in this way, when it is not desirable that the data group to be determined having a smaller distribution representative point area or a smaller data point distribution area is determined as a relevant data group, it may become possible to remove such a data group to be determined.

Further, when this process using the distribution representative point area threshold value is performed before it is determined whether there is the overlapping area, it may not be necessary to perform the process determining whether there is the overlapping area on the data group to be determined having a smaller distribution representative point area or a smaller data point distribution area.

Further, in the determination step, it may be further determined whether an area of the overlapping area is equal to or greater than a predetermined overlapping area point area threshold value, and when determining that the area of the overlapping area is equal to or greater than the overlapping area threshold value, it may be determined that the data group to be determined is the relevant data group.

By doing in this way, when it is not desirable that the data group to be determined having a smaller overlapping area is determined as a relevant data group, it may become possible to remove such a data group to be determined.

Further, in the determination step, it may be further determined whether a ratio of an area of the overlapping area to an area of the determination area is equal to or greater than a predetermined first ratio threshold value, and when determining that the ratio of the area of the overlapping area to the area of the determination area is equal to or greater than the predetermined first ratio threshold value, it may be determined that the data group to be determined is the relevant data group.

By doing in this way, when it is not desirable that the data group to be determined having a smaller ratio of the area of the overlapping area to the area of the determination area is determined as a relevant data group, it may become possible to remove such a data group to be determined.

Further, in the determination step, it may be further determined whether a ratio of an area of the overlapping area to an area of the distribution representative point area is equal to or greater than a predetermined second ratio threshold value, and when determining that the ratio of the area of the overlapping area to the area of the distribution representative point area is equal to or greater than the predetermined second ratio threshold value, it may be determined that the data group to be determined is the relevant data group.

By doing in this way, when it is not desirable that the data group to be determined having a smaller ratio of the area of the overlapping area to the area of the distribution representative point area is determined as a relevant data group, it may become possible to remove such a data group to be determined.

Further, in the determination step, the distribution representative point area may be defined by sequentially connecting the representative points with lines in a manner such that the lines are not crossed over each other.

By doing in this way, it may become possible to define the distribution representative point area in accordance with the contour of the data point distribution area.

Further, in the distribution representative point selection step, a center or a gravity center of the data point distribution area of the data group to be determined may be selected as the division center point. By doing in this way, when the steps of the embodiment of the present invention are executed by a computer, it may become possible to automatically set division center point adapted to the data group to be determined without manual setting the division center point by an operator.

Further, in the distribution representative point selection step, when there is a divided area including no data point, the division center point may be selected as the representative point. By doing in this way, it may become possible to define more appropriate distribution representative point area in accordance with the contour of the data point distribution area when compared with a case where the division center point is not selected as the representative point.

Further, in the distribution representative point selection step, after the representative points are selected, two divided areas adjoining each other are set as a consideration area, in the consideration area, vectors starting from the division center point and terminating at the data points are provided, from among the data points having magnitudes of a component of the vectors, the magnitudes being greater than magnitudes of the component of the representative points, the component referring a direction parallel to an extending direction of a line that starts from the division center point and that contacts the two divided areas of the consideration area; a data point having the greatest magnitude is added as the representative point. By doing in this way, it may become possible to define more appropriate distribution representative point area in accordance with the contour of the data point distribution area.

Further, when there are two or more data points having the greatest magnitude of the component in the consideration area, the data point closest to the division center point may be added as the representative point. By doing in this way, from among two or more data points having the greatest magnitude of the component in the consideration area, it may become possible to select the data point closest to the line contacting the two divided areas of the consideration area, thereby enabling defining more appropriate distribution representative point area in accordance with the contour of the data point distribution area.

Further, in the distribution representative point selection step, after the representative points are selected, vectors starting from the division center point and terminating at the data points are provided, in each of the directions parallel to extending directions of the lines that start from the division center point and that are used to divide the area on the coordinate plane into the divided areas, from among the data points having magnitudes of the component of the vectors, the magnitudes being greater than magnitudes of the component of the representative points, a data point having the greatest magnitude is added as the representative point. By doing in this way as well, it may become possible to define more appropriate distribution representative point area in accordance with the contour of the data point distribution area.

Further, when there are two or more data points having the greatest magnitude in the direction parallel to extending direction of the line that starts from the division center point and that is used to divide the area on the coordinate plane into the divided areas, the data point closest to the division center point may be added as the representative point. By doing in this way, from among two or more data points having the greatest magnitude of the component in the consideration area, it may become possible to select the data point closest to the line contacting the two divided areas of the consideration area, thereby enabling defining more appropriate distribution representative point area in accordance with the contour of the data point distribution area.

According to an embodiment of the present invention, there is provided a non-transitory computer-readable recording medium, including a program encoded and stored in a computer readable format to cause a computer to execute the steps described above. By using the recording medium, due to the program, it may become possible to cause a computer to execute the steps of the identification method according to an embodiment of the present invention.

Although the invention has been described with respect to specific embodiments for a complete and clear disclosure, the appended claims are not to be thus limited but are to be construed as embodying all modifications and alternative constructions that may occur to one skilled in the art that fairly fall within the basic teachings herein set forth.

For example, the figures are used for the description of the embodiments of the present invention. However, the figures may not be always necessary in any of the steps. Namely, with the information of the determination area and the data group of the plural data having two variables as a pair, each of the steps may be performed.

Further, in the above embodiments, an XY orthogonal coordinate plane is used. However, as a coordinate plane used in the present invention, the oblique coordinate plane may also be used.

The present invention may also be used for identifying whether the data group is distributed in a specific area, the data group including plural data having two variables as a pair.

What is claimed is:

1. An identification method performed by a computer to identify a data point distribution area on a coordinate plane, the identification method comprising:
   a distribution representative point selection step of:
      dividing an area on the coordinate plane into two or more divided areas in a manner such that the divided areas radiate from a division center point, the division center point being an arbitrary point and a center point of the divide areas, plural data being expressed as data points on the coordinate plane, the plural data constituting a data group to be determined, each of the plural data including two variables as a pair, the data point distribution area being a distribution area of the data points, and
      selecting, in each of the divided areas, from among the data points in the divided area, a data point having the greatest distance from the division center point as a representative point of the data point distribution area; and
   a determination step of:
      determining whether there is an overlapping area where a distribution representative point area overlaps a determination area, the distribution representative point area being defined by connecting the representative points with lines, the determination area being a specific area set on the coordinate plane, and
      determining, when there is the overlapping area, that the data group to be determined is a relevant data group.

2. The identification method according to claim 1, wherein the data group to be determined any one of pattern defect inspection result data, particle inspection result data, and wafer test result data in a semiconductor device manufacturing process.

3. The identification method according to claim 1, further comprising:
   a representative point information registration step of associating and registering information of the representative points acquired in the distribution representative point selection step with information to be used to identifying the data group to be determined into a database, wherein
   the representative point information registration step is performed before the determination step is performed, and
   in the determination step, it is determined whether there is the overlapping area by reading the information of the representative points associated with the information to be used to identify the data group to be determined from the database.

4. The identification method according to claim 3, wherein
   in the representative point information registration step, characteristic information is associated with the information to be used to identify the data group to be determined and stored in the database, the characteristic information including a distribution range of the data point distribution area, a distribution range of the distribution representative point area, and at least one of an area, a roundness rate, and a data point distribution density of the distribution representative point area, and
   in the determination step, after making a short list of the data groups to be determined based on the characteristic information, it is determined whether there is the overlapping area.

5. The identification method according to claim 1, wherein
   in the determination step, it is determined whether an area of the distribution representative point area is equal to or greater than a predetermined distribution representative point area threshold value, and
   when determining that the area of the distribution representative point area is less than the distribution representative point area threshold value, it is determined that the data group to be determined is not the relevant data group.

6. The identification method according to claim 1, wherein
   in the determination step, it is further determined whether an area of the overlapping area is equal to or greater than a predetermined overlapping area threshold value, and
   when determining that the area of the overlapping area is equal to or greater than the overlapping area threshold value, it is determined that the data group to be determined is the relevant data group.

7. The identification method according to claim 1, wherein
   in the determination step, it is further determined whether a ratio of an area of the overlapping area to an area of the determination area is equal to or greater than a predetermined first ratio threshold value, and
   when determining that the ratio of the area of the overlapping area to the area of the determination area is equal to or greater than the predetermined first ratio threshold value, it is determined that the data group to be determined is the relevant data group.

8. The identification method according to claim 1, wherein
   in the determination step, it is further determined whether a ratio of an area of the overlapping area to an area of the distribution representative point area is equal to or greater than a predetermined second ratio threshold value, and when determining that the ratio of the area of the overlapping area to the area of the distribution representative point area is equal to or greater than the predetermined second ratio threshold value, it is determined that the data group to be determined is the relevant data group.

9. The identification method according to claim 1, wherein
in the determination step, the distribution representative point area is defined by sequentially connecting the representative points with lines in a manner such that the lines are not crossed over each other.

10. The identification method according to claim 1, wherein
in the distribution representative point selection step, a center or a gravity center of the data point distribution area of the data group to be determined is selected as the division center point.

11. The identification method according to claim 1, wherein
in the distribution representative point selection step, when there is a divided area including no data point, the division center point is selected as the representative point.

12. The identification method according to claim 1, wherein
in the distribution representative point selection step, after the representative points are selected, two divided areas adjoining each other are set as a consideration area; in the consideration area, vectors starting from the division center point and terminating at the data points are provided, from among the data points having magnitudes of a component of the vectors, the magnitudes being greater than magnitudes of the component of the representative points, the component referring a direction parallel to an extending direction of a line that starts from the division center point and that contacts the two divided areas of the consideration area; and a data point having the greatest magnitude is added as the representative point.

13. The identification method according to claim 12, wherein
when there are two or more data points having the greatest magnitude of the component in the consideration area, the data point closest to the division center point is added as the representative point.

14. The identification method according to claim 1, wherein
in the distribution representative point selection step, after the representative points are selected, vectors starting from the division center point and terminating at the data points are provided, in each of the directions parallel to extending directions of the lines that start from the division center point and that are used to divided the area on the coordinate plane into the divided areas; and from among the data points having magnitudes of the component of the vectors, the magnitudes being greater than magnitudes of the component of the representative points, a data point having the greatest magnitude is added as the representative point.

15. The identification method according to claim 14, wherein
when there are two or more data points having the greatest magnitude in the direction parallel to the extending direction of the line that starts from the division center point and that are used to divide the area on the coordinate plane into the divided areas, the data point closest to the division center point is added as the representative point.

16. A non-transitory computer-readable recording medium, comprising a program encoded and stored in a computer readable format to cause a computer to execute an identification method for identifying a data point distribution area on a coordinate plane. the identification method comprising:

a distribution representative point selection step of:
dividing an area on the coordinate plane into two or more divided areas in a manner such that the divided areas radiate from a division center point, the division center point being an arbitrary point and a center point of the divide areas, plural data being pressed as data points on the coordinate plane, the plural data constituting a data group to be determined each of the plural data including two variables as a pair, the data point distribution area being a distribution area of the data points, and selecting, in each of the divided areas, from among the data points in the divided area, a data point having the greatest distance from the division center point as a representative point of the data point distribution area; and a determination step of:
determining whether there is an overlapping area where a distribution representative point area overlaps a determination area the distribution representative point area being defined by connecting the representative points with lines, the determination area being a specific area set on the coordinate plane, and determining, when there is the overlapping area, that the data group to be determined is a relevant data group.

* * * * *